(12) United States Patent
Uzawa et al.

(10) Patent No.: US 9,182,585 B2
(45) Date of Patent: Nov. 10, 2015

(54) ENDOSCOPE OBJECTIVE LENS

(71) Applicant: OLYMPUS CORPORATION, Tokyo (JP)

(72) Inventors: Tsutomu Uzawa, Saitama (JP); Tsutomu Sasamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/189,006

(22) Filed: Feb. 25, 2014

(65) Prior Publication Data

US 2014/0204475 A1 Jul. 24, 2014

Related U.S. Application Data

(63) Continuation of application No. PCT/JP2013/074640, filed on Sep. 12, 2013.

(30) Foreign Application Priority Data

Sep. 14, 2012 (JP) .................. 2012-202689

(51) Int. Cl.
*G02B 23/24* (2006.01)
*G02B 15/02* (2006.01)
*G02B 15/10* (2006.01)
*A61B 1/00* (2006.01)

(52) U.S. Cl.
CPC ............ *G02B 23/243* (2013.01); *A61B 1/0011* (2013.01); *A61B 1/00096* (2013.01); *A61B 1/00188* (2013.01); *G02B 15/02* (2013.01); *G02B 15/10* (2013.01)

(58) Field of Classification Search
CPC ........ G02B 15/02; G02B 15/04; G02B 15/10; G02B 15/22; G02B 15/177; G02B 23/243

USPC .......... 359/672–675, 738, 739–74, 686, 689, 359/691, 693, 749, 751–756, 761–763, 359/770–771, 781–784, 790, 381; 600/175–176
See application file for complete search history.

(56) References Cited

U.S. PATENT DOCUMENTS 4,157,211 A * 6/1979 Tanaka et al. .................. 359/674
5,547,457 A * 8/1996 Tsuyuki et al. ................ 600/175

FOREIGN PATENT DOCUMENTS

| JP | 06-222263 | 8/1994 |
| JP | 07-072387 | 3/1995 |
| JP | 3251076 | 1/2002 |
| JP | 2010-128459 | 6/2010 |
| JP | 4653823 | 3/2011 |
| JP | 2011-227421 | 11/2011 |

* cited by examiner

*Primary Examiner* — Thomas K Pham
*Assistant Examiner* — Marin Pichler
(74) *Attorney, Agent, or Firm* — Kenyon & Kenyon LLP

(57) ABSTRACT

An object is to provide an endoscope objective lens in which the aberrations are less susceptible to manufacturing errors and in which the variation in field curvature caused by focusing is small. There is provided an endoscope objective lens including: in sequence from an object side, a front group having negative refractive power, an aperture stop, and a rear group having positive refractive power; and a focusing lens that has a negative refractive power and that can be inserted into an optical path between the front group and the rear group. The focusing lens is inserted into the optical path in a normal observation state and is retracted from the optical path in a short-distance observation state, in which the working distance is smaller than that in the normal observation state.

4 Claims, 26 Drawing Sheets

US 9,182,585 B2

ENDOSCOPE OBJECTIVE LENS

This is a continuation of International Application PCT/JP2013/074640, with an international filing date of Sep. 12, 2013, which is hereby incorporated by reference herein in its entirety. This application claims the benefit of Japanese Patent Application No. 2012-202689, the content of which is incorporated herein by reference.

TECHNICAL FIELD

The present invention relates to an endoscope objective lens and, more specifically, to an endoscope objective lens that has a focusing function.

BACKGROUND ART

Conventionally, various focusing methods have been proposed for small, simple objective lenses suitable for endoscopes (for example, see PTLs 1 to 3). In PTL 1, focusing is achieved by moving some lenses of an objective-lens optical system in the optical axis direction. In PTL 2, a wire is used to move a lens. In PTL 3, removable parallel plates are disposed near an aperture stop, and, by switching between parallel plates having different thicknesses, a shift of the focal position caused by a difference in the wavelength used is corrected.

In a typical focusing method, like that employed in PTL 1, the position of image formation is corrected by moving, in the optical axis direction, a lens having refractive power.

The function of a focusing lens will be described from the standpoint of aberration correction. In an image-forming relationship for a certain object distance, a focusing lens, which is moved for focusing, shares the aberration correction with other lens elements. The ratio of this sharing is determined according to the refractive power, the surface shape, and the height and angle of rays, especially according to the refractive power. In this image-forming relationship, when manufacturing errors, particularly eccentricity errors, such as an error occurring in a direction perpendicular to the optical axis of the lens elements (shifting) or an error associated with tilting of the lens elements (tilting), occur, the sharing ratio of the aberration correction changes, causing asymmetric bokeh or the like, which makes the aberrations worse. The contribution ratio of the focusing lens and the other lens elements to the deterioration of the aberrations is determined according to, in particular, the refractive power, like the sharing ratio of the aberration correction. Hence, if a lens having higher refractive power becomes eccentric, the degree of deterioration of the aberrations tends to be greater.

In the means for moving the lens disclosed in PTL 2, a certain amount of slack has to be provided to facilitate sliding, which leads to eccentricity of the focusing lens. Furthermore, because the point of application of a force with the wire is displaced from the point of action of the lens, the focusing lens tends to become eccentric when moving on the optical axis in the focusing operation (during focusing). In particular, in recent years, with an increase in number of pixels of image sensors, the deterioration of aberrations due to manufacturing errors, such as eccentricity, has become more apparent.

In PTL 3, the focal position is moved not by changing the working distance, but, when observation is performed at a predetermined working distance, by switching the parallel plates having different thicknesses to correct a shift in focal position due to the wavelength used. Therefore, the focal position can only be moved by a very small distance, small enough to correct an axial chromatic aberration of the objective lens.

Objective lenses of endoscopes, which employs the conventional focusing methods, are intended to achieve a wide angle of view with a simple configuration; hence, they have large negative distortion. If focusing is performed with such an objective lens, the image plane is tilted in the minus (under) direction when the working distance changes from the long side to the short side.

CITATION LIST

Patent Literature

{PTL 1} The Publication of Japanese Patent No. 4653823
{PTL 2} The Publication of Japanese Patent No. 3251076
{PTL 3} Japanese Unexamined Patent Application, Publication No. 2010-128459

SUMMARY OF INVENTION

The present invention provides an endoscope objective lens including: in sequence from the object side, a front group having negative refractive power, an aperture stop, and a rear group having positive refractive power; and a focusing lens that has negative refractive power and that can be inserted into or retracted from an optical path between the front group and the rear group. The focusing lens is inserted into the optical path in a normal observation state and is retracted from the optical path in a short-distance observation state, in which the working distance is smaller than that in the normal observation state.

DESCRIPTION OF EMBODIMENTS

Figure 1:
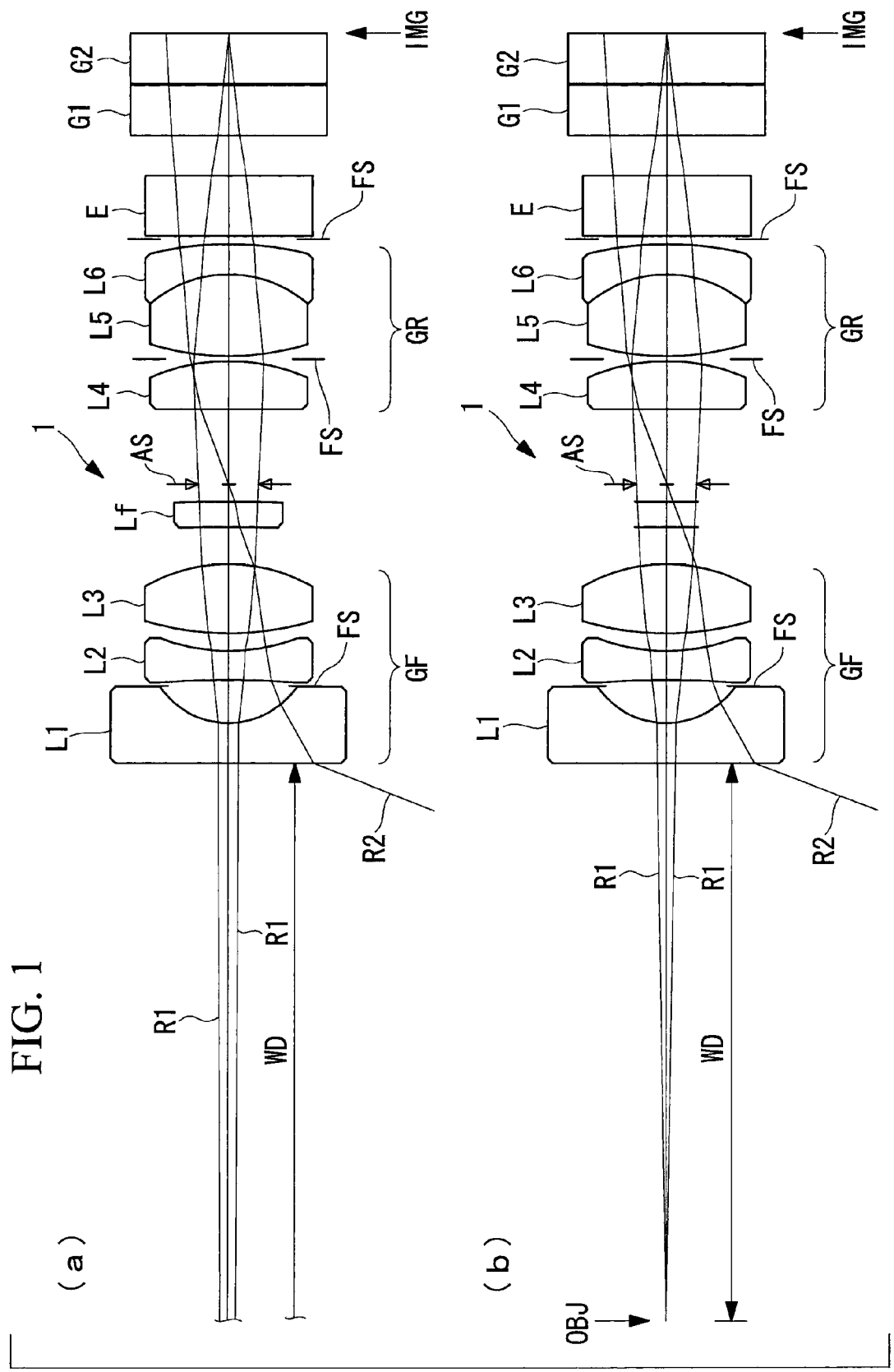
FIG. 1 includes lens cross-sections showing the overall configuration of an endoscope objective lens according to an embodiment of the present invention, showing (a) a normal observation state in which a focusing lens is inserted into an optical path and (b) a short-distance observation state in which the focusing lens is retracted from the optical path.
Figure 2:
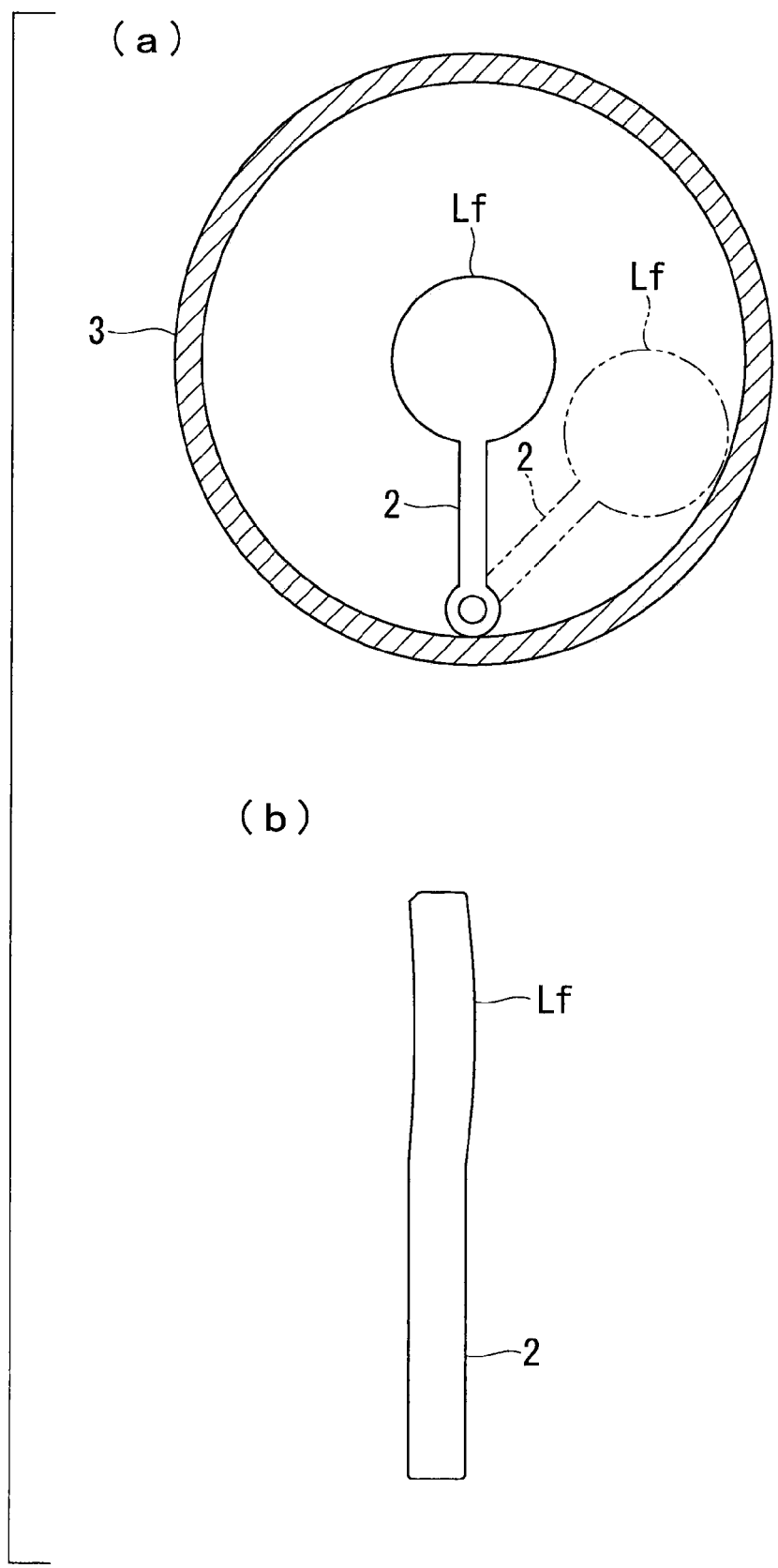
FIG. 2 includes (a) a front view and (b) a side view, respectively, showing an example arm member for supporting the focusing lens.

Referring to FIGS. 1 and 2, an endoscope objective lens 1 according to an embodiment of the present invention will be described below.

As illustrated in FIG. 1(a), the endoscope objective lens 1 according to this embodiment includes, in sequence from the object side, a front group GF, an aperture stop AS, and a rear group GR. The endoscope objective lens 1 further includes a focusing lens Lf that is provided in such a manner that it can be inserted into or retracted from an optical path between the front group GF and the rear group GR.

In the figures, reference sign OBJ denotes an object plane, reference sign IMG denotes an image plane, reference sign R1 denotes an axial marginal ray, and reference sign R2 denotes a principal ray at the maximum angle of view.

The front group GF includes, in sequence from the object side, a plano-concave lens (first lens) L1 having a flat surface facing the object side, a biconcave lens (second lens) L2, and a biconvex lens L3. The front group GF has negative refractive power.

The rear group GR includes, in sequence from the object side, a plano-convex lens L4 having a flat surface facing the object side, a biconvex lens L5, and a negative meniscus lens L6 having a concave surface facing the object side. The rear group GR has positive refractive power. The biconvex lens L5 and the negative meniscus lens L6 are combined.

Note that the number and shape of the lenses constituting the front group GF and the rear group GR are not limited to those presented above and may be appropriately changed.

The endoscope objective lens 1 further optionally includes a flare stop FS, an optical component E, such as an infrared cut filter or an optical low-pass filter, a CCD cover glass G1, and a CCD chip sealing glass G2.

The focusing lens Lf has negative refractive power and is, preferably, a meniscus lens. In the normal observation state, the focusing lens Lf is disposed in the optical path such that the concave surface thereof faces the object side and such that the optical axis thereof is aligned with the optical axis of the endoscope objective lens 1, as illustrated in FIG. 1(a). On the other hand, in the short-distance observation state, the focusing lens Lf is retracted from the optical path, as illustrated in FIG. 1(b). In the short-distance observation state, in which the focusing lens Lf does not exist in the optical path, a working distance WD of the endoscope objective lens 1 is smaller than that in the normal observation state. Hence, the focal point moves in a direction toward the first lens L1, enabling short-distance observation.

The relationship between the presence/absence of the focusing lens Lf in the optical path and the working distance WD is explained by the diverging effect of the focusing lens Lf. More specifically, considering a change in position of the object point with respect to the image point depending on the presence/absence of the focusing lens Lf, when the focusing lens Lf is on the optical axis, because of the diverging effect thereof, focusing on a far object is achieved. On the other hand, when the focusing lens Lf is not on the optical axis, because of the absence of the diverging effect thereof, focusing on a near object is achieved.

The endoscope objective lens 1 of the this embodiment which employs the above-described focusing method, is characterized in that the aberrations are less susceptible to manufacturing errors. An eccentricity error occurring when the focusing lens Lf is attached needs to be taken into consideration only in the normal observation state, in which the focusing lens Lf is on the optical axis. In the short-distance observation state, in which the focusing lens Lf is not on the optical axis, because the focusing lens Lf is retracted from the optical path, deterioration in performance due to the eccentricity error does not occur. It is possible to employ a configuration in which the focusing lens Lf is urged to a prescribed position of the frame when the focusing lens Lf is located on the optical axis. Thus, the eccentricity error is less likely to occur.

Note that, in this embodiment, "focus" means to correct the movement of the focal position due to a change in working distance and to maintain the focal position constant. It means, for example, to bring the endoscope objective lens, which is focused on a far observation target, closer to the observation target and make it focus on the observation target, and it has the same meaning as "to bring something in focus" or "to focus on something".

Furthermore, in the present invention, a lens group that is moved for focusing is called the "focusing lens".

The endoscope objective lens 1 satisfies the following Conditional Expressions (1) to (6).

$$-230 < fc/FL < -10 \quad (1)$$

$$0.7 < (rb+ra)/(rb-ra) < 20 \quad (2)$$

$$-120 < ra/FL < -3 \quad (3)$$

$$0.25 < (r2f+r1b)/(r2f-r1b) < 1 \quad (4)$$

$$-50 < r2f/FL < -2 \quad (5)$$

$$0.5 < r1b/FL < 3 \quad (6)$$

where fc is the focal length of the focusing lens Lf, FL is the focal length of the entire endoscope objective lens 1 with the focusing lens Lf inserted into the optical path, ra is the radius of curvature of an object-side surface of the focusing lens Lf, rb is the radius of curvature of the image-side surface of the focusing lens Lf, r2f is the radius of curvature of the object-side surface of the second lens L2, and r1b is the radius of curvature of the image-side surface of the first lens L1.

Conditional Expression (1) relates to manufacturing errors and the amount of correction of the focus, and it defines the focal length fc of the focusing lens Lf. When fc/FL is higher than or equal to −10, which is the upper limit of Conditional Expression (1), the degree of influence of the eccentricity error on the optical performance deterioration is large, which is undesirable. More specifically, even though the eccentricity error is the same, asymmetric bokeh etc. tend to occur. When fc/FL is lower than or equal to −230, which is the lower limit of Conditional Expression (1), the degree of influence of the eccentricity error on the optical performance deterioration is small. However, the amount of correction of the focus is small, which is undesirable. More specifically, the focusing range decreases.

Note that the endoscope objective lens 1 according to this embodiment desirably satisfies (1'), more desirably (1"), and most desirably (1''').

$$-230 < fc/FL < -50 \quad (1')$$

$$-230 < fc/FL < -90 \quad (1'')$$

$$-200 < fc/FL < -90 \quad (1''')$$

Conditional Expressions (2) and (3) relate to variation of aberrations caused by focusing and define the shape of the focusing lens Lf. When (rb+ra)/(rb−ra) is lower than or equal to 0.7, which is the lower limit of Conditional Expression (2), or when ra/FL is lower than or equal to −120, which is the lower limit of Conditional Expression (3), the image plane is tilted in the minus (under) direction in the short-distance observation state, which is undesirable. When (rb+ra)/(rb−ra) is higher than or equal to 20, which is the upper limit of Conditional Expression (2), or when ra/FL is higher than or equal to −3, which is upper limit of Conditional Expression (3), the difference (astigmatic difference) between the sagittal image plane and the meridional image plane is large, which is undesirable.

Note that the endoscope objective lens 1 according to this embodiment desirably satisfies (3'), more desirably (3"), and most desirably (3'''), as follows:

$$-120 < ra/FL < -10 \quad (3')$$

$$-120 < ra/FL < -20 \quad (3'')$$

$$-70 < ra/FL < -20 \quad (3''')$$

Conditional Expressions (4), (5), and (6) relate to reduction in size of the front group GF and define the lens shape of the lens end portion. When (r2f+r1b)/(r2f−r1b) is lower than or equal to 1, which is the upper limit of Conditional Expression (4), when r2f/FL is lower than or equal to −50, which is the lower limit of Conditional Expression (5), or when r1b/FL is lower than or equal to 0.5, which is the lower limit of Conditional Expression (6), the lens diameter of the front group GF tends to increase, which is undesirable. It is also disadvantageous for increasing the angle of view. When (r2f+r1b)/(r2f−r1b) is higher than or equal to 0.25, which is the lower limit of Conditional Expression (4), when r2f/FL is higher than or equal to −2, which is the upper limit of Conditional Expression (5), or when r1b/FL is higher than or equal to 3, which is the upper limit of Conditional Expression (6), although it is advantageous for reducing the lens diameter of the front group GF, high-order off-axis aberrations tend to occur, which is undesirable. Note that, an optical filter, such as an infrared cut filter, may be disposed between the first lens L1 and the second lens L2.

Note that the endoscope objective lens 1 according to this embodiment desirably satisfies (5'), and more desirably (5"), as follows:

$$-30 < r2f/FL < -2 \quad (5')$$

$$-10 < r2f/FL < -2 \quad (5'')$$

Furthermore, this configuration desirably satisfies (6'), more desirably (6"), and most desirably (6'''), as follows:

$$0.5 < r1b/FL < 3 \quad (6')$$

$$0.5 < r1b/FL < 2 \quad (6'')$$

$$1 < r1b/FL < 2 \quad (6''')$$

FIG. 2(a) shows an example driving mechanism that moves the focusing lens Lf between an inserted position (shown by a solid line) and a retracted position (shown by a two-dot chain line). The driving mechanism has an arm member 2 at one end, which supports the focusing lens Lf, and a motor (not shown) that rotates the other end of the arm member 2 to swing the focusing lens Lf. Reference numeral 3 denotes a lens barrel accommodating the endoscope objective lens 1.

The focusing lens Lf is a molded lens, and the arm member 2 and the focusing lens Lf are integrally molded. A meniscus lens is mainly used as the focusing lens Lf. By using a molded lens as the meniscus lens constituting the focusing lens LF, the focusing lens Lf can be manufactured easily and at low cost, compared with a case where the meniscus lens is formed by polishing. FIG. 2(b) is a diagram showing the integrally molded focusing lens Lf and arm member 2, as viewed from the side. By molding the focusing lens Lf and the arm member 2 integrally, a frame member for supporting the focusing lens Lf does not need to be provided at the outer circumference of the focusing lens Lf, and hence, the diameter can be reduced. In addition, a space for accommodating the retracted focusing lens Lf can be reduced.

In the thus-configured endoscope objective lens 1, the aberrations are less susceptible to manufacturing errors, and the variation in field curvature caused by focusing is small. Hence, it is possible to stably obtain high-quality images.

EXAMPLES

Next, examples of the above-described endoscope objective lens according to this embodiment will be described below, with reference to FIGS. 3 to 26.

In lens data presented in the respective examples, r is the radius of curvature, d is the surface distance, nd is the refractive index at the d-line, vd is the Abbe number at the d-line, OBJ is the object plane, and IMG is the image plane. The lens data is data in the normal observation state, including the focusing lens inserted into the optical path. Numerical values that differ between the normal observation state and the short-distance observation state (e.g., the working distance d0; the radius of curvatures ri and ri+1 of i-th and i+1-th surfaces (corresponding to the lens surface of the focusing lens); and the refractive index and Abbe number of a medium GLAi filling the space between the i-th and i+1-th surfaces (when the medium is air, it will be indicated "air") will be shown in Miscellaneous Data. The surface numbers corresponding to the aperture stop, the flare stop, the optical component, the CCD cover glass, and the CCD chip sealing glass are accompanied by reference numerals AS, FS, E, G1, and G2, respectively.

The lens cross-sections to be referred to show the lens configurations in the normal state, including the focusing lens inserted into the optical path. In the lens cross-sections, the optical axis direction of the endoscope objective lens is assumed to be direction Z, and the image height direction is assumed to be direction Y. Furthermore, reference numeral R1 denotes an axial marginal ray, and reference numeral R2 denotes a principal ray at the maximum angle of view.

In the aberration diagrams to be referred to, (a) shows distortion, (b) shows chromatic aberration of magnification, (c) shows astigmatism, and (d) shows spherical aberration. In (c), a solid line shows the astigmatism in the sagittal image plane, and a chain line shows the astigmatism in the meridional image plane.

Example 1

Figure 3:
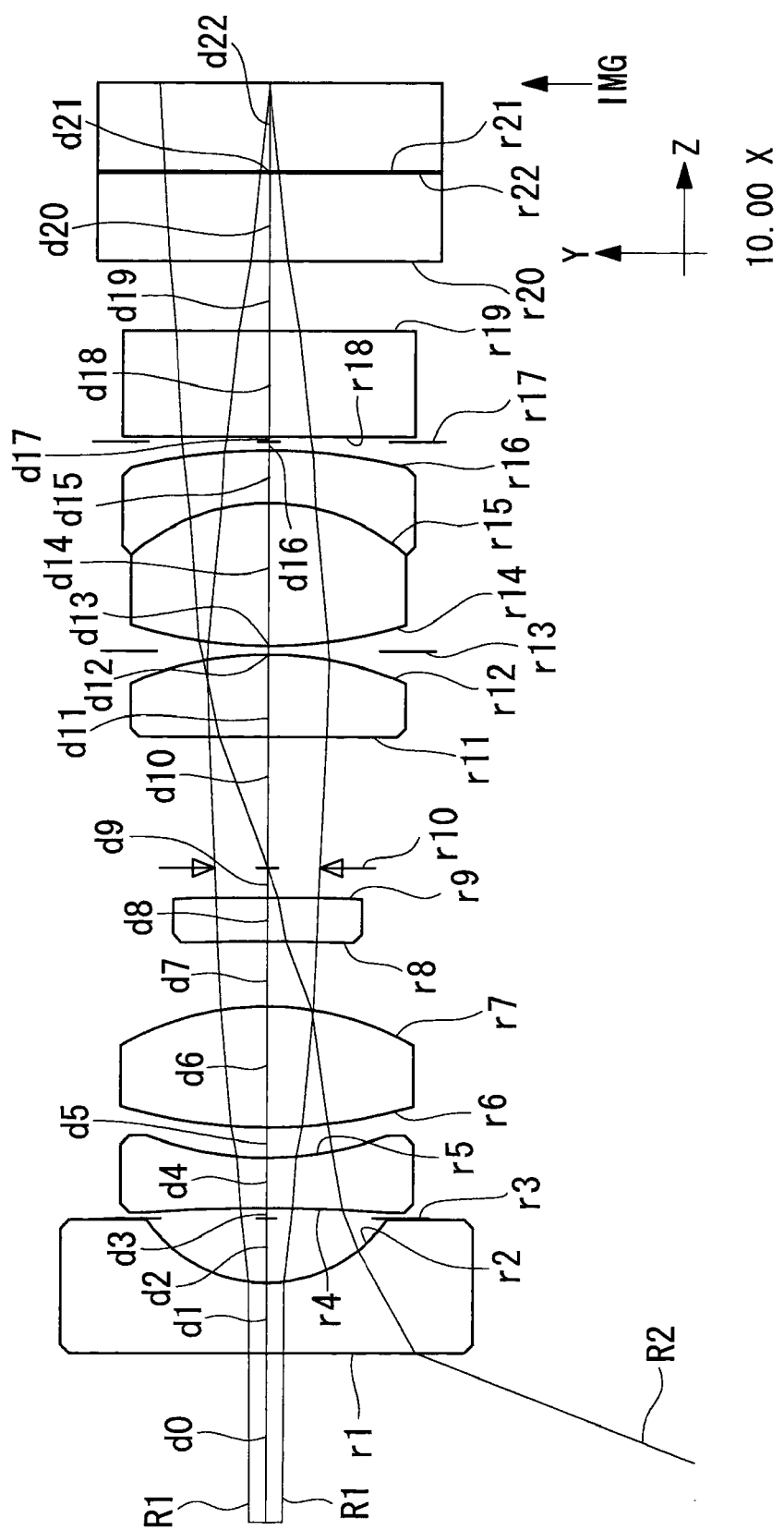
FIG. 3 is a lens cross-section showing the overall configuration (in the normal observation state) of an endoscope objective lens according to Example 1 of the present invention.

The lens configuration of an endoscope objective lens according to Example 1 of this embodiment is shown in FIG. 3.

In this example, the front group includes, in sequence from the object side, a plano-concave lens (first lens) having a flat surface facing the object side, a biconcave lens (second lens), and a biconvex lens. The rear group includes, in sequence from the object side, a plano-convex lens having a flat surface facing the object side, a biconvex lens, and a negative meniscus lens having a concave surface facing the object side. In the rear group, the biconvex lens and the negative meniscus lens are combined.

A focusing lens (eighth surface) is a negative meniscus lens that has a concave surface facing the object side and that is inserted into or retracted from the optical path between the front group and the aperture stop.

Figure 4:
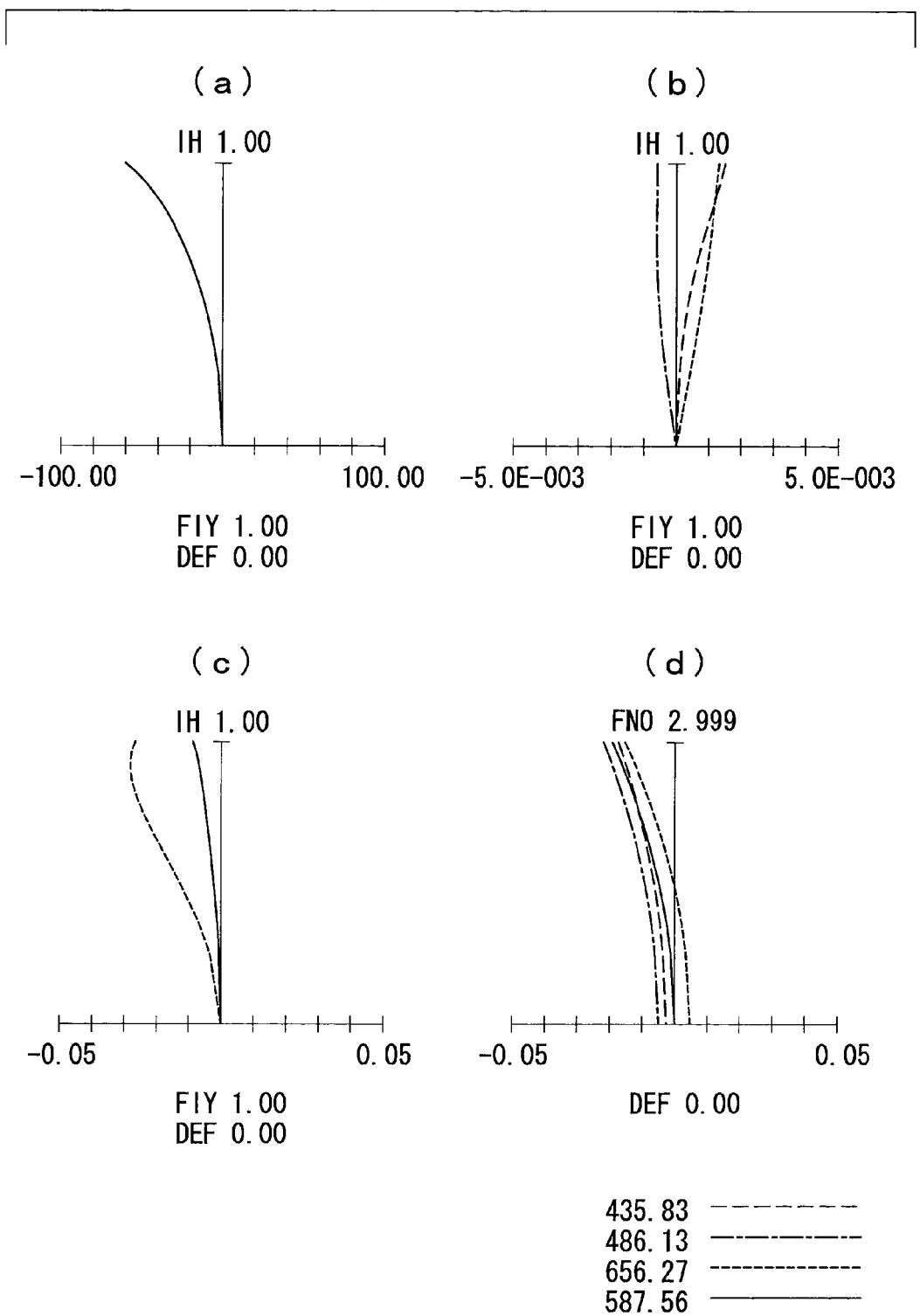
FIG. 4 includes aberration diagrams showing (a) distortion, (b) chromatic aberration of magnification, (c) astigmatism, and (d) spherical aberration, respectively, of the endoscope objective lens, in the normal observation state, according to Example 1 of the present invention.
Figure 5:
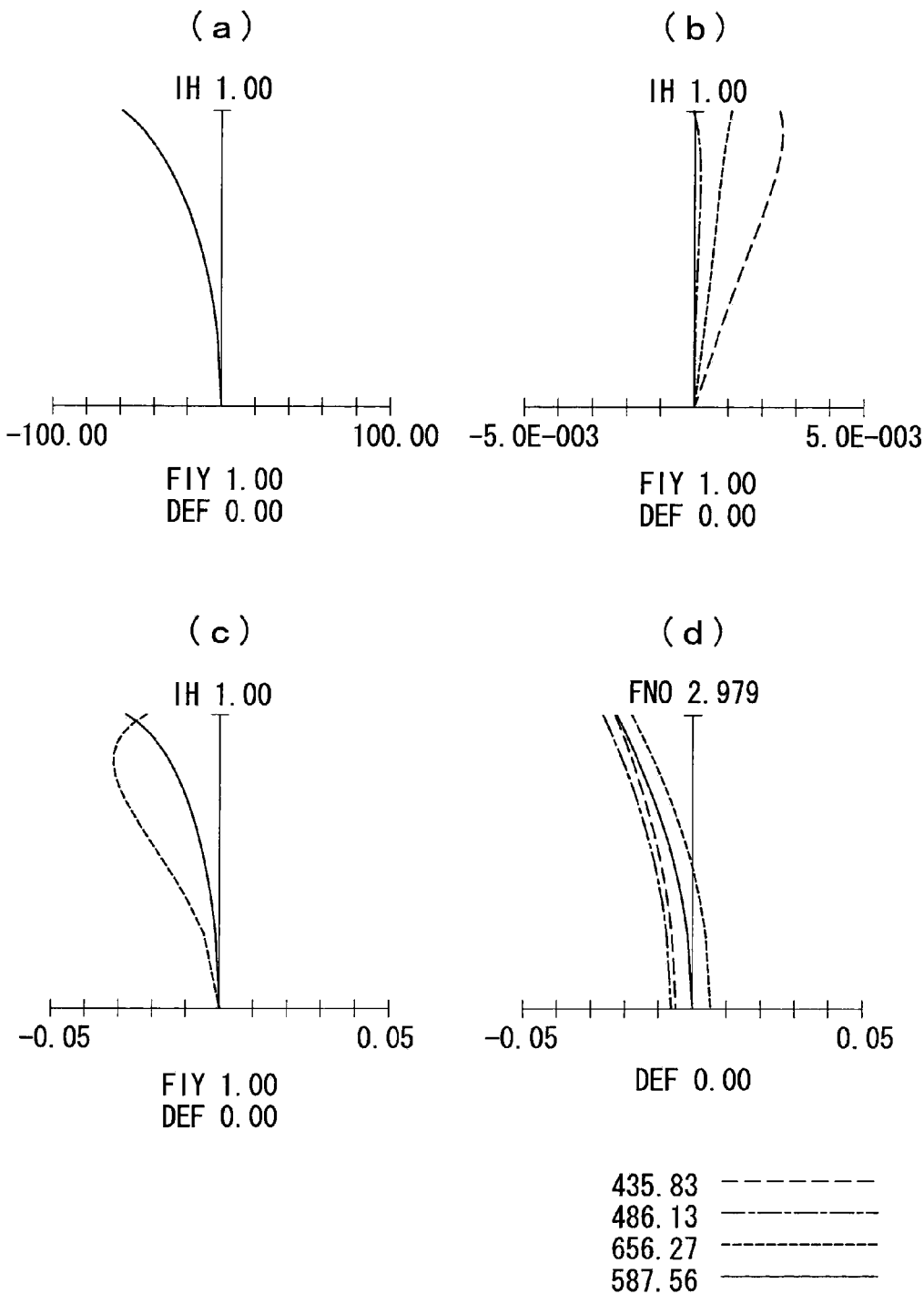
FIG. 5 includes aberration diagrams showing (a) distortion, (b) chromatic aberration of magnification, (c) astigmatism, and (d) spherical aberration, respectively, of the endoscope objective lens, in the short-distance observation state, according to Example 1 of the present invention.

The aberration diagrams of the thus-configured endoscope objective lens according to this example, in the normal observation state and in the short-distance observation state, are shown in FIGS. 4 and 5.

Lens Data

| surface number | r | d | nd | vd |
|---|---|---|---|---|
| OBJ | ∞ | 30.0000 (d0) | 1. | |
| 1 | ∞ | 0.6238 | 1.88300 | 40.76 |
| 2 | 1.3366 | 0.5758 | 1. | |
| 3 (FS) | ∞ | 0.0930 | 1. | |
| 4 | −15.4125 | 0.4520 | 1.88300 | 40.76 |
| 5 | 3.0857 | 0.2676 | 1. | |
| 6 | 4.6793 | 1.0834 | 1.69895 | 30.13 |
| 7 | −2.6759 | 0.5759 | 1. | |
| 8 | −21.7597 (r8) | 0.3899 | 1.88300 (GLA8) | 40.76 |
| 9 | −28.0944 (r9) | 0.2651 | 1. | |
| 10 (AS) | ∞ | 1.1697 | 1. | |
| 11 | ∞ | 0.7390 | 1.69680 | 55.53 |
| 12 | −3.1521 | 0.0312 | 1. | |
| 13 (FS) | ∞ | 0.0468 | 1. | |
| 14 | 4.2780 | 1.2638 | 1.65160 | 58.55 |
| 15 | −1.9266 | 0.4679 | 1.92286 | 18.90 |
| 16 | −5.2633 | 0.0780 | 1. | |
| 17 (FS) | ∞ | 0.0468 | 1. | |
| 18 (E) | ∞ | 0.9357 | 1.51800 | 75.00 |
| 19 | ∞ | 0.6263 | 1 | |
| 20 (G1) | ∞ | 0.7798 | 1.51633 | 64.14 |
| 21 | ∞ | 0.0156 | 1.51300 | 63.01 |
| 22 (G2) | ∞ | 0.7798 | 1.50600 | 60.00 |
| IMG | ∞ | 0. | | |

Miscellaneous Data

| | normal observation state | short-distance observation state |
|---|---|---|
| d0 | 30.0000 | 8.7000 |
| r8 | −21.75966 | ∞ |

-continued

|  | normal observation state | short-distance observation state |
|---|---|---|
| r9 | −28.09439 | ∞ |
| GLA8 | nd: 1.88300<br>vd: 40.76 | air |

Example 2

Figure 6:
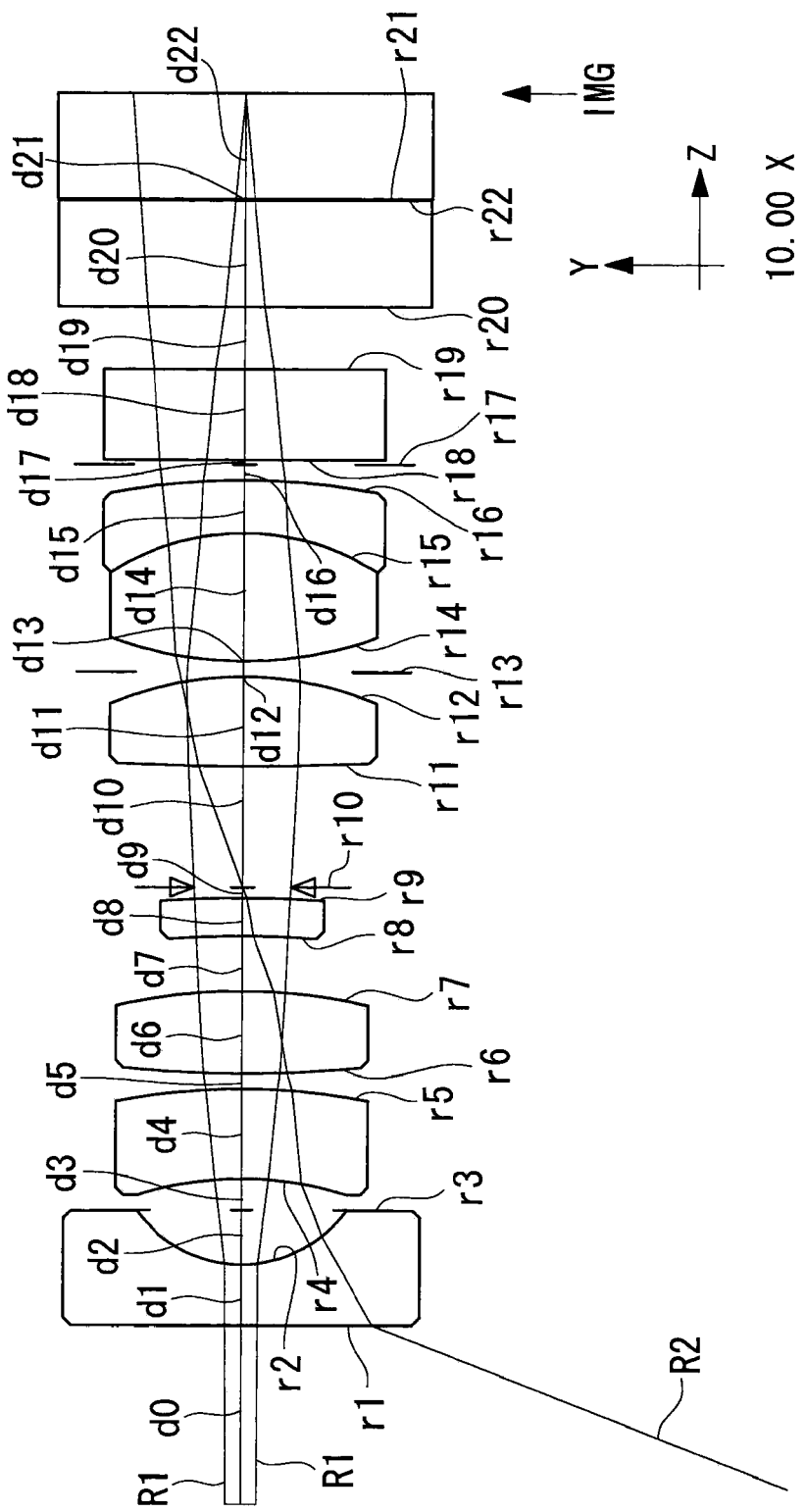
FIG. 6 is a lens cross-section showing the overall configuration (in the normal observation state) of an endoscope objective lens according to Example 2 of the present invention.

The lens configuration of an endoscope objective lens according to Example 2 of this embodiment is shown in FIG. 6.

In this example, the front group includes, in sequence from the object side, a plano-concave lens (first lens) having a flat surface facing the object side, a negative meniscus lens (second lens) having a concave surface facing the object side, and a biconvex lens. The rear group includes two biconvex lenses and a negative meniscus lens having a concave surface facing the object side, and the biconvex lens on the image side and the negative meniscus lens are combined.

The focusing lens (eighth surface) is a negative meniscus lens that has a concave surface facing the object side and that is inserted into or retracted from the optical path between the front group and the aperture stop.

Figure 7:
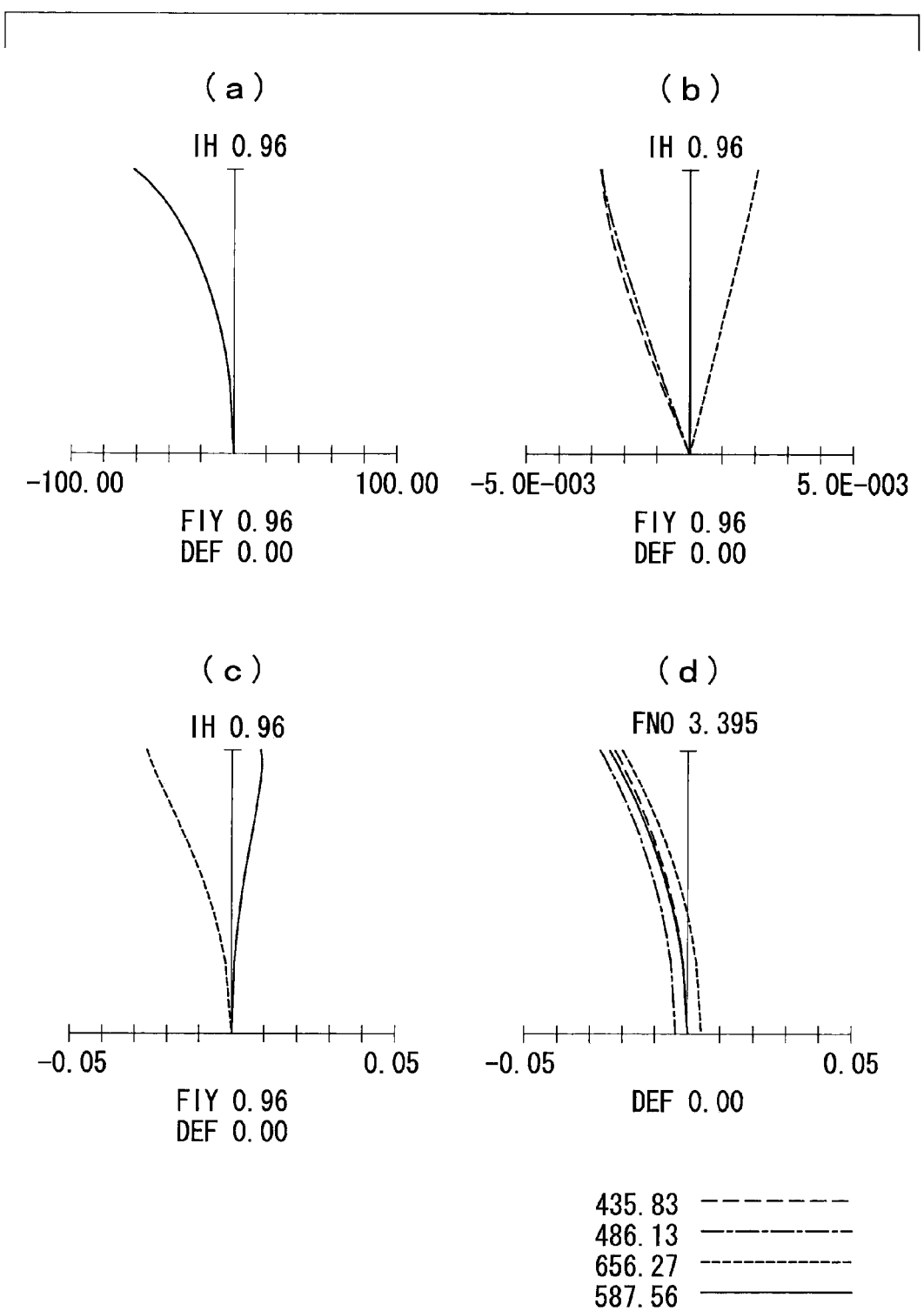
FIG. 7 includes aberration diagrams showing (a) distortion, (b) chromatic aberration of magnification, (c) astigmatism, and (d) spherical aberration, respectively, of the endoscope objective lens, in the normal observation state, according to Example 2 of the present invention.
Figure 8:
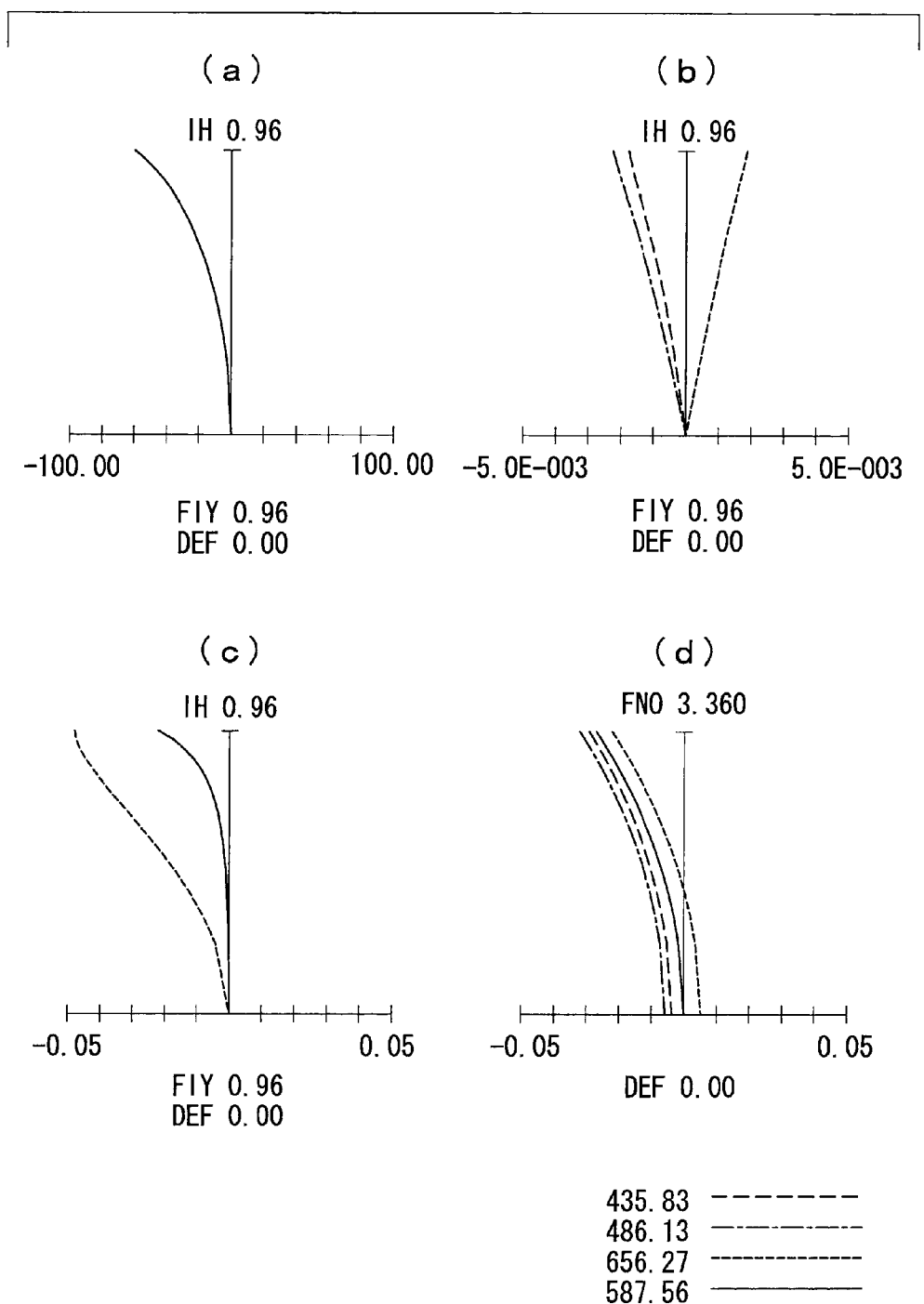
FIG. 8 includes aberration diagrams showing (a) distortion, (b) chromatic aberration of magnification, (c) astigmatism, and (d) spherical aberration, respectively, of the endoscope objective lens, in the short-distance observation state, according to Example 2 of the present invention.

The aberration diagrams of the thus-configured endoscope objective lens according to this example, in the normal observation state and in the short-distance observation state, are shown in FIGS. 7 and 8.

Lens Data

| surface number | r | d | nd | vd |
|---|---|---|---|---|
| OBJ | ∞ | 24.0000<br>(d0) | 1. |  |
| 1 | ∞ | 0.5069 | 1.88300 | 40.76 |
| 2 | 1.1077 | 0.4562 | 1. |  |
| 3 (FS) | ∞ | 0.2661 | 1. |  |
| 4 | −2.9644 | 0.7604 | 1.92286 | 18.90 |
| 5 | −5.5764 | 0.1267 | 1. |  |
| 6 | 10.5406 | 0.6970 | 1.84666 | 23.78 |
| 7 | −4.7006 | 0.4623 | 1. |  |
| 8 | −8.6485<br>(r8) | 0.3168 | 1.88300<br>(GLA8) | 40.76 |
| 9 | −10.0780<br>(r9) | 0.0887 | 1. |  |
| 10 (AS) | ∞ | 1.0139 | 1. |  |
| 11 | 23.8606 | 0.7604 | 1.65160 | 58.55 |
| 12 | −2.8896 | 0.0380 | 1. |  |
| 13 (FS) | ∞ | 0.0887 | 1. |  |
| 14 | 3.3217 | 1.0773 | 1.58913 | 61.14 |
| 15 | −2.1127 | 0.4436 | 1.92286 | 18.90 |
| 16 | −6.0136 | 0.1267 | 1. |  |
| 17 (FS) | ∞ | 0.0380 | 1. |  |
| 18 (E) | ∞ | 0.7604 | 1.51800 | 75.00 |
| 19 | ∞ | 0.5235 | 1. |  |
| 20 (G1) | ∞ | 0.8872 | 1.51633 | 64.14 |
| 21 | ∞ | 0.0127 | 1.51300 | 63.01 |
| 22 (G2) | ∞ | 0.8872 | 1.50600 | 60.00 |
| IMG | ∞ | 0. |  |  |

Miscellaneous Data

|  | normal observation state | short-distance observation state |
|---|---|---|
| d0 | 24.0000 | 7.2000 |
| r8 | −8.64846 | ∞ |

-continued

|  | normal observation state | short-distance observation state |
|---|---|---|
| r9 | −10.07804 | ∞ |
| GLA8 | nd: 1.88300<br>vd: 40.76 | air |

Example 3

Figure 9:
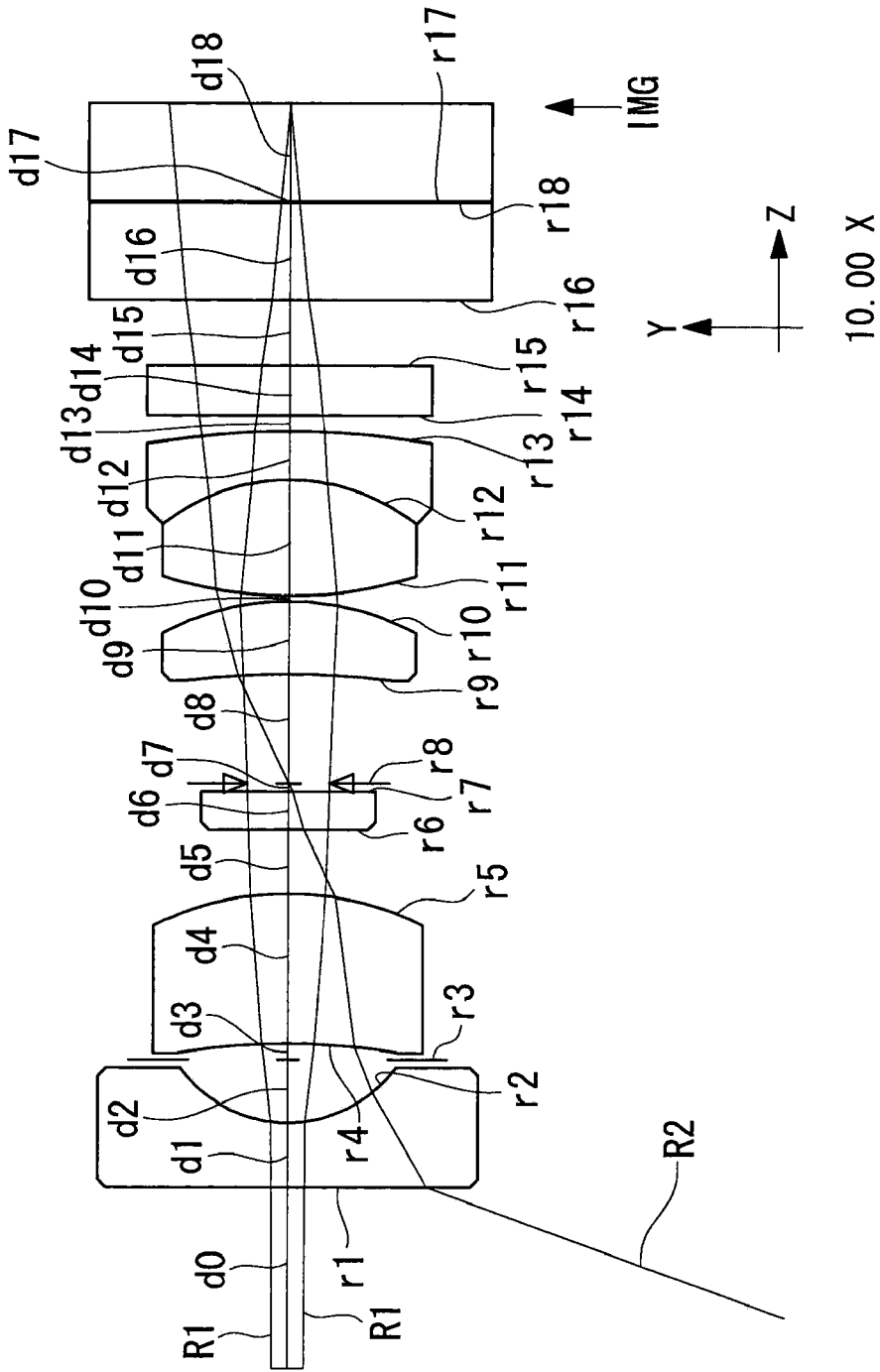
FIG. 9 is a lens cross-section showing the overall configuration (in the normal observation state) of an endoscope objective lens according to Example 3 of the present invention.

The lens configuration of an endoscope objective lens according to Example 3 of this embodiment is shown in FIG. 9.

In this example, the front group includes, in sequence from the object side, a plano-concave lens (first lens) having a flat surface facing the object side, and a positive meniscus lens (second lens) having a concave surface facing the object side. The rear group includes, in sequence from the object side, a positive meniscus lens having a concave surface facing the object side, a biconvex lens, and a negative meniscus lens having a concave surface facing the object side. In the rear group, the biconvex lens and the positive meniscus lens are combined.

The focusing lens (sixth surface) is a plano-concave lens that has a flat surface facing the image side and that is inserted into or retracted from the optical path between the front group and the aperture stop.

Figure 10:
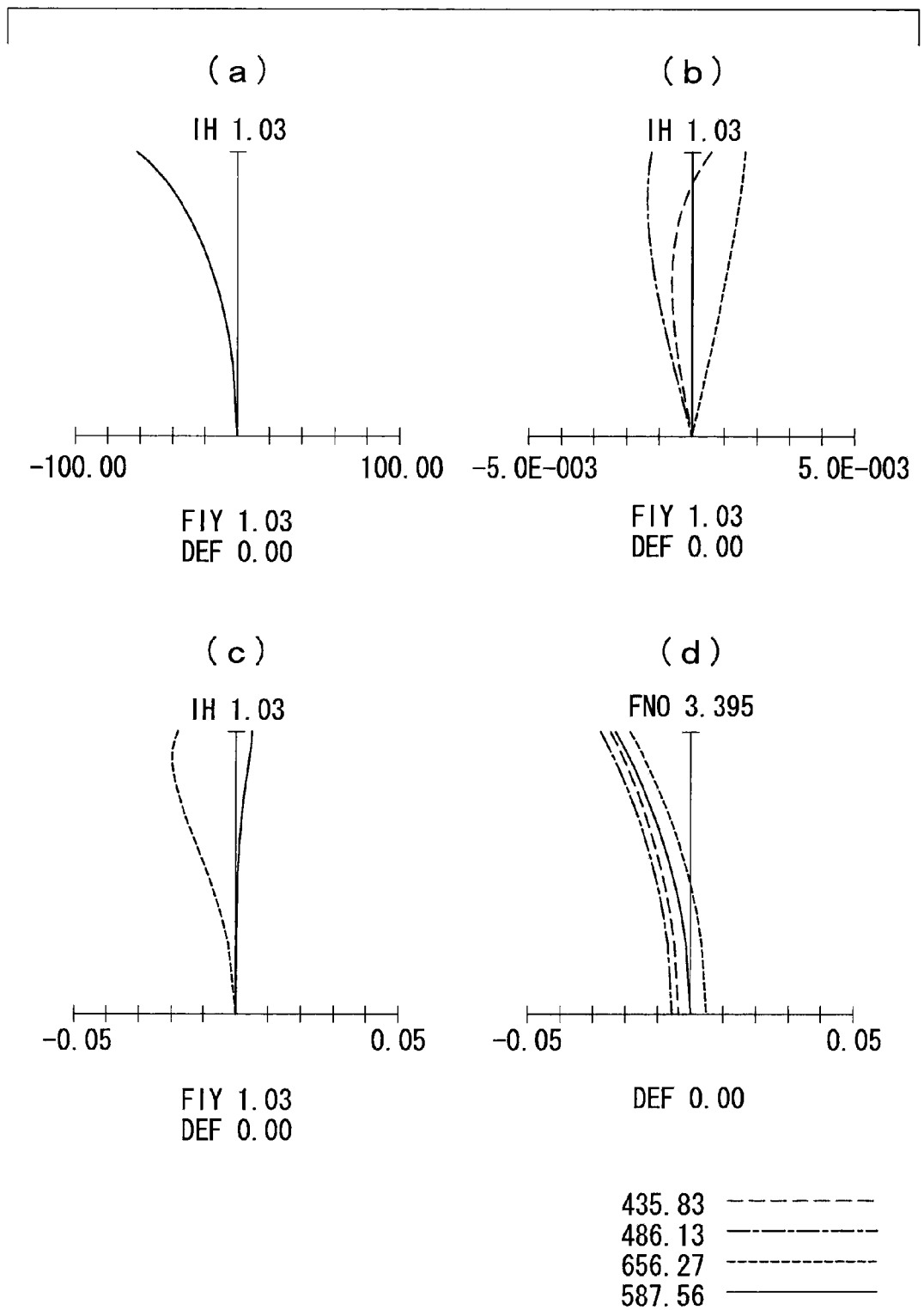
FIG. 10 includes aberration diagrams showing (a) distortion, (b) chromatic aberration of magnification, (c) astigmatism, and (d) spherical aberration, respectively, of the endoscope objective lens, in the normal observation state, according to Example 3 of the present invention.
Figure 11:
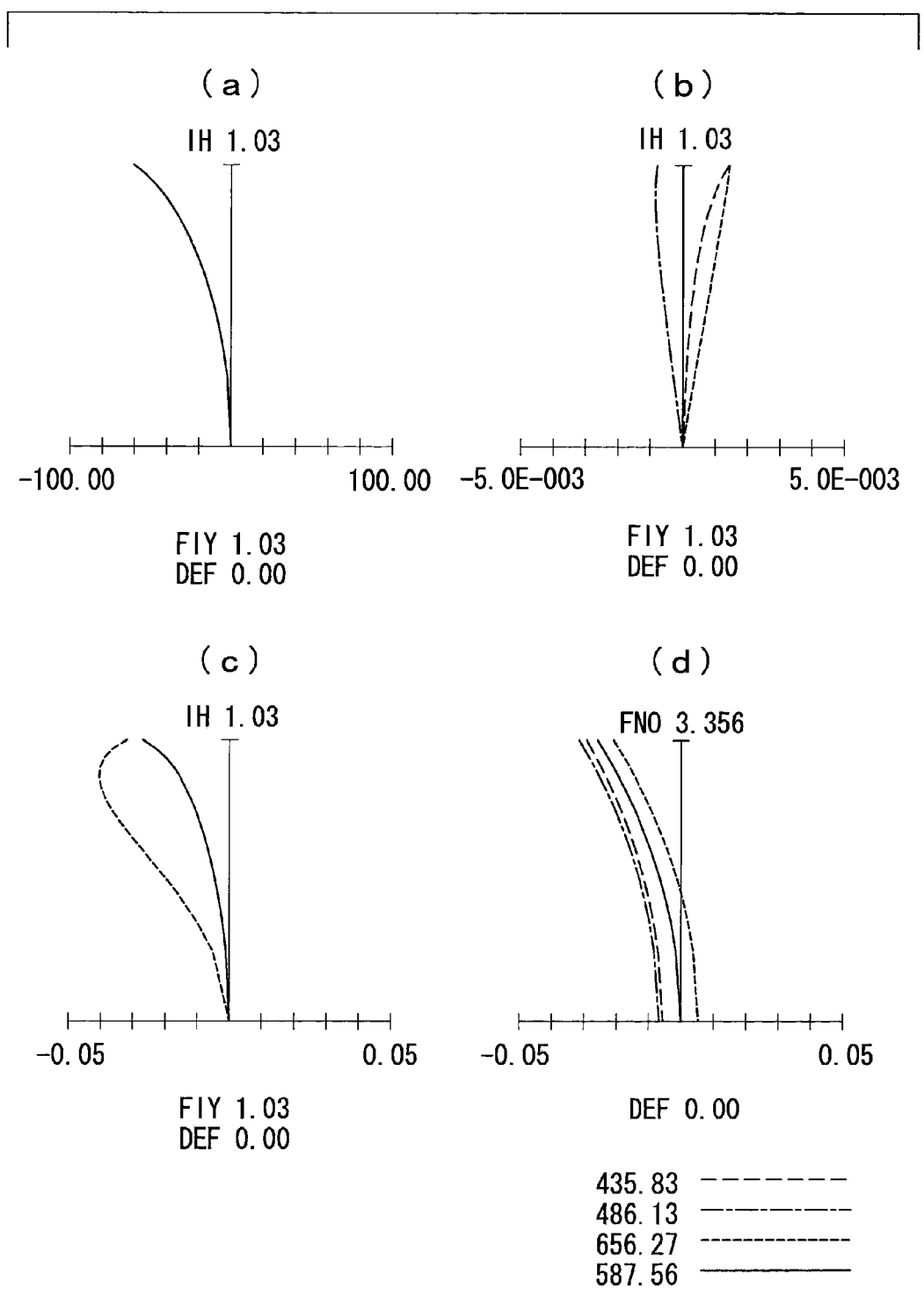
FIG. 11 includes aberration diagrams showing (a) distortion, (b) chromatic aberration of magnification, (c) astigmatism, and (d) spherical aberration, respectively, of the endoscope objective lens, in the short-distance observation state, according to Example 3 of the present invention.

The aberration diagrams of the thus-configured endoscope objective lens according to this example, in the normal observation state and in the short-distance observation state, are shown in FIGS. 10 and 11.

Lens Data

| surface number | r | d | nd | vd |
|---|---|---|---|---|
| OBJ | ∞ | 25.0000<br>(d0) | 1. |  |
| 1 | ∞ | 0.5353 | 1.88300 | 40.76 |
| 2 | 1.1348 | 0.5233 | 1. |  |
| 3 (FS) | ∞ | 0.1337 | 1. |  |
| 4 | −5.5758 | 1.2513 | 2.00330 | 28.27 |
| 5 | −2.5855 | 0.5342 | 1. |  |
| 6 | −34.9936<br>(r6) | 0.3156 | 1.48749<br>(GLA6) | 70.23 |
| 7 | ∞<br>(r7) | 0.0669 | 1. |  |
| 8 (AS) | ∞ | 0.9056 | 1. |  |
| 9 | −7.1090 | 0.6044 | 1.88300 | 40.76 |
| 10 | −2.2737 | 0.0439 | 1. |  |
| 11 | 3.6328 | 0.9594 | 1.69680 | 55.53 |
| 12 | −1.7382 | 0.4014 | 1.92286 | 18.90 |
| 13 | −7.3173 | 0.1338 | 1. |  |
| 14 (E) | ∞ | 0.4148 | 1.51633 | 64.14 |
| 15 | ∞ | 0.5432 | 1. |  |
| 16 (G1) | ∞ | 0.8029 | 1.51633 | 64.14 |
| 17 | ∞ | 0.0134 | 1.51300 | 63.01 |
| 18 (G2) | ∞ | 0.8029 | 1.50600 | 60.00 |
| IMG | ∞ | 0. |  |  |

Miscellaneous Data

|  | normal observation state | short-distance observation state |
|---|---|---|
| d0 | 25.0000 | 7.5000 |
| r6 | −34.99361 | ∞ |
| r7 | ∞ | ∞ |
| GLA6 | nd: 1.48749<br>vd: 70.23 | air |

Example 4

Figure 12:
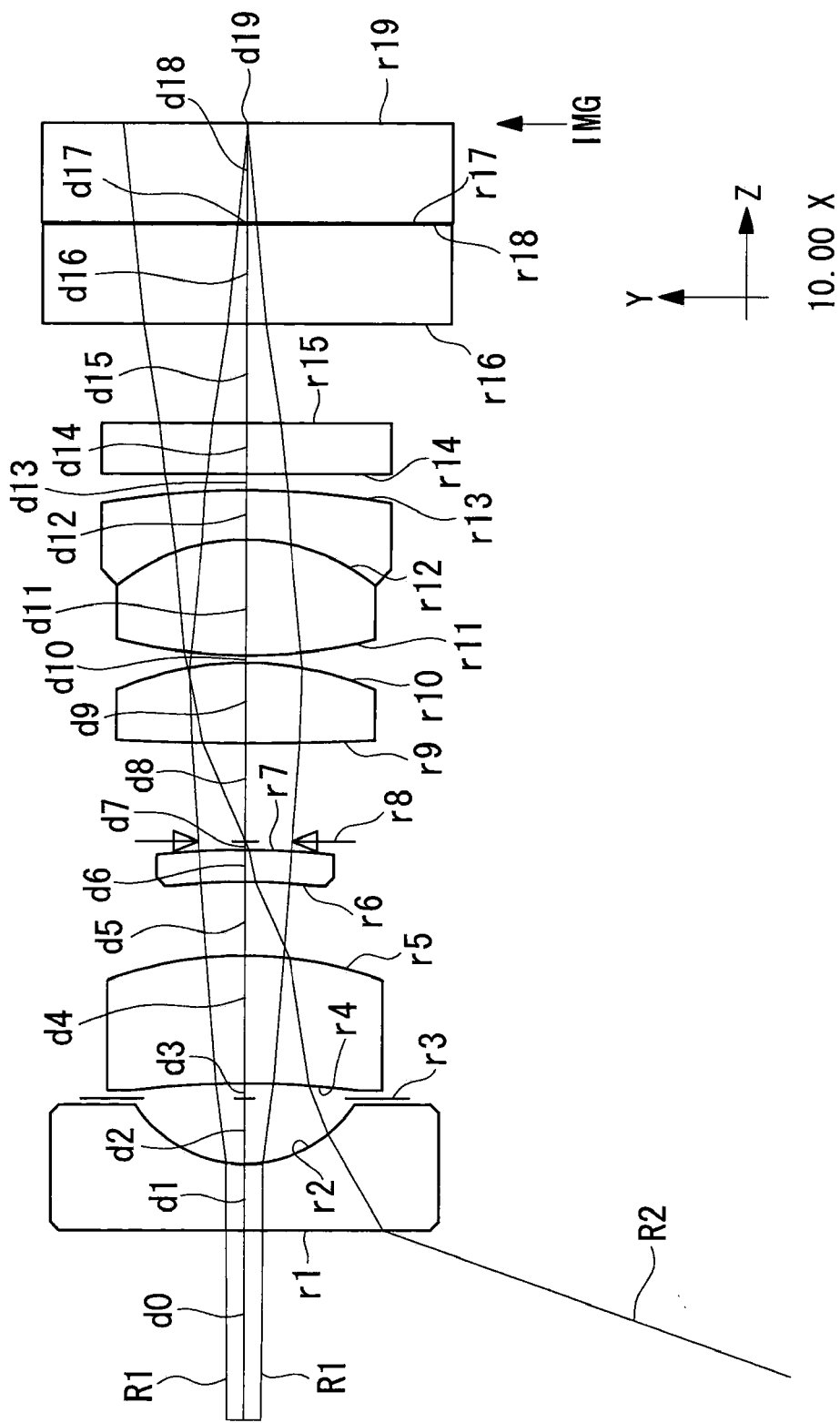
FIG. 12 is a lens cross-section showing the overall configuration (in the normal observation state) of an endoscope objective lens according to Example 4 of the present invention.

The lens configuration of an endoscope objective lens according to Example 4 of this embodiment is shown in FIG. 12.

In this example, the front group includes, in sequence from the object side, a plano-concave lens (first lens) having a flat surface facing the object side, and a positive meniscus lens (second lens) having a concave surface facing the object side. The rear group includes, in sequence from the object side, two biconvex lenses and a negative meniscus lens having a concave surface facing the object side. In the rear group, the biconvex lens on the image side and the negative meniscus lens are combined.

The focusing lens (sixth surface) is a negative meniscus lens that has a concave surface facing the object side and that is inserted into or retracted from the optical path between the front group and the aperture stop.

Figure 13:
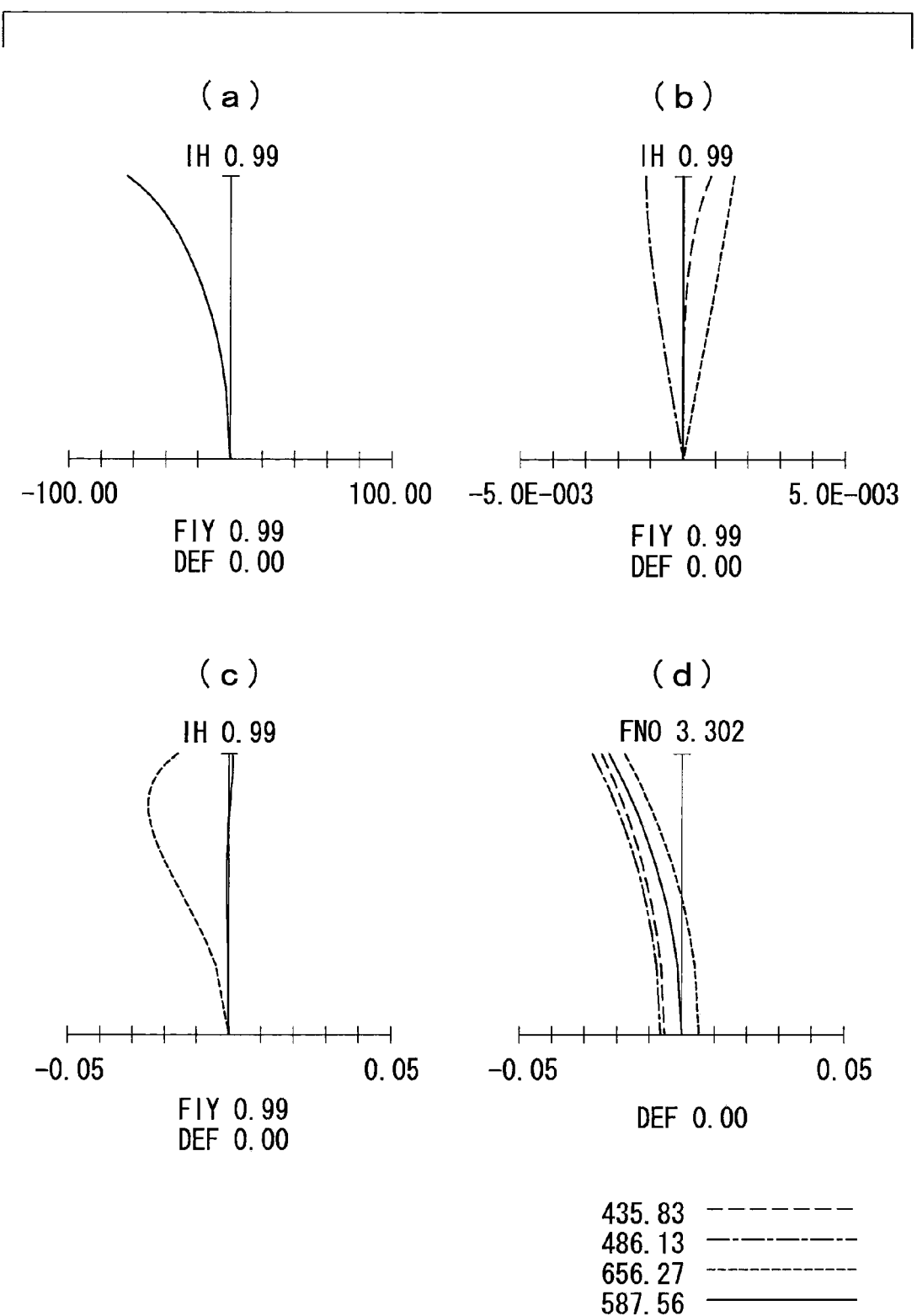
FIG. 13 includes aberration diagrams showing (a) distortion, (b) chromatic aberration of magnification, (c) astigmatism, and (d) spherical aberration, respectively, of the endoscope objective lens, in the normal observation state, according to Example 4 of the present invention.
Figure 14:
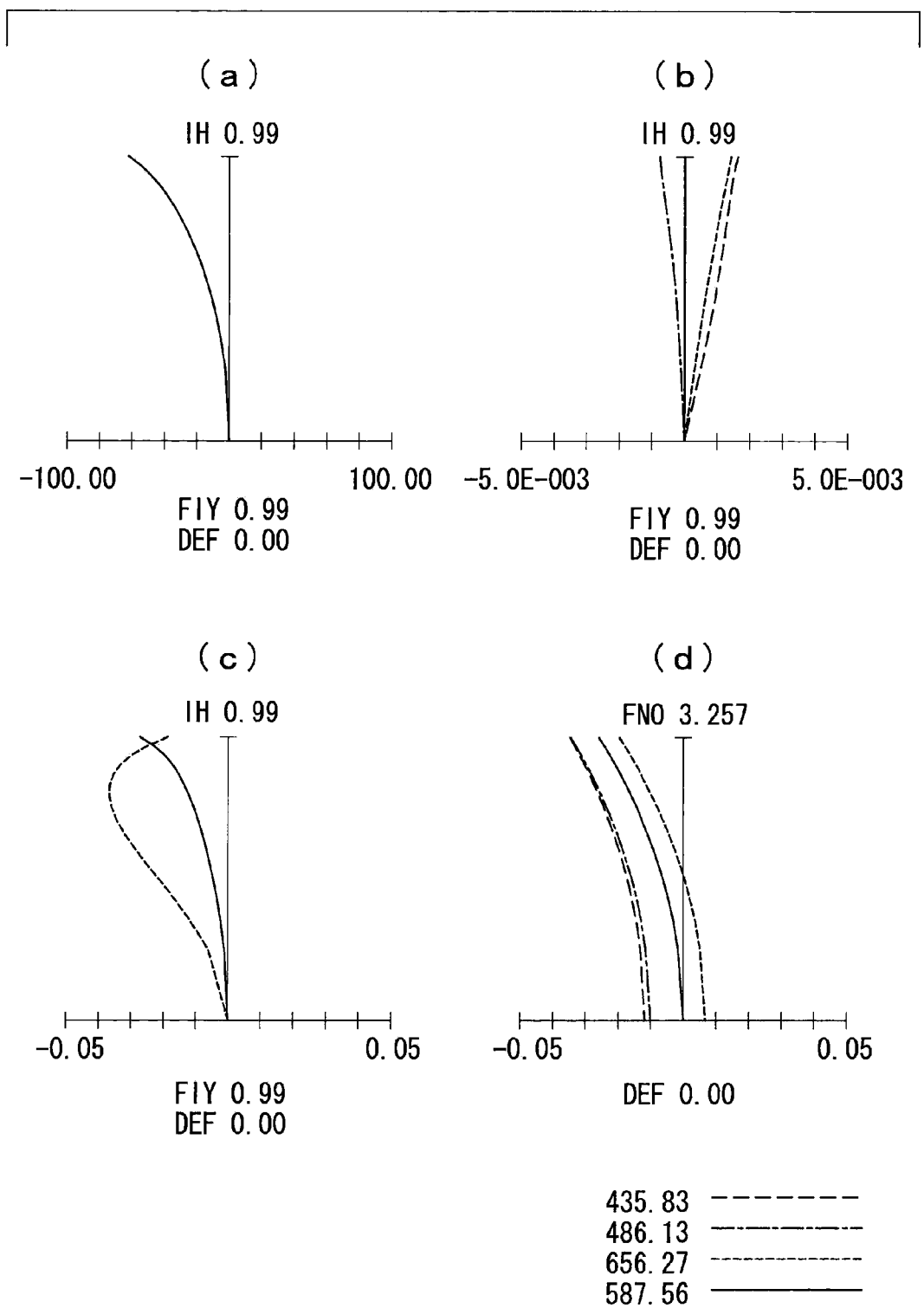
FIG. 14 includes aberration diagrams showing (a) distortion, (b) chromatic aberration of magnification, (c) astigmatism, and (d) spherical aberration, respectively, of the endoscope objective lens, in the short-distance observation state, according to Example 4 of the present invention.

The aberration diagrams of the thus-configured endoscope objective lens according to this example, in the normal observation state and in the short-distance observation state, are shown in FIGS. 13 and 14.

Lens Data

| surface number | r | d | nd | vd |
|---|---|---|---|---|
| OBJ | ∞ | 24.0000 (d0) | 1. | |
| 1 | ∞ | 0.5174 | 1.88300 | 40.76 |
| 2 | 1.0649 | 0.5156 | 1. | |
| 3 (FS) | ∞ | 0.1203 | 1. | |
| 4 | −7.2757 | 1.0012 | 1.92286 | 18.90 |
| 5 | −3.2252 | 0.5821 | 1. | |
| 6 | −5.6126 (r6) | 0.2546 | 1.92286 (GLA6) | 18.90 |
| 7 | −6.4197 (r7) | 0.0647 | 1. | |
| 8 (AS) | ∞ | 0.7736 | 1. | |
| 9 | 23.1334 | 0.6333 | 1.88300 | 40.76 |
| 10 | −2.6059 | 0.0569 | 1. | |
| 11 | 4.3225 | 0.9048 | 1.65160 | 58.55 |
| 12 | −1.6704 | 0.3881 | 1.92286 | 18.90 |
| 13 | −6.5845 | 0.1294 | 1. | |
| 14 (E) | ∞ | 0.4010 | 1.51633 | 64.14 |
| 15 | ∞ | 0.7783 | 1. | |
| 16 | ∞ | 0.7761 | 1.51633 | 64.14 |
| 17 (G1) | ∞ | 0.0129 | 1.51300 | 63.01 |
| 18 | ∞ | 0.7761 | 1.50600 | 60.00 |
| 19 (G2) | ∞ | 0. | 1. | |
| IMG | ∞ | 0. | | |

Miscellaneous Data

| | normal observation state | short-distance observation state |
|---|---|---|
| d0 | 24.0000 | 7.3000 |
| r6 | −5.61259 | ∞ |
| r7 | −6.41971 | ∞ |
| GLA6 | nd: 1.92286 vd: 18.90 | air |

Example 5

Figure 15:
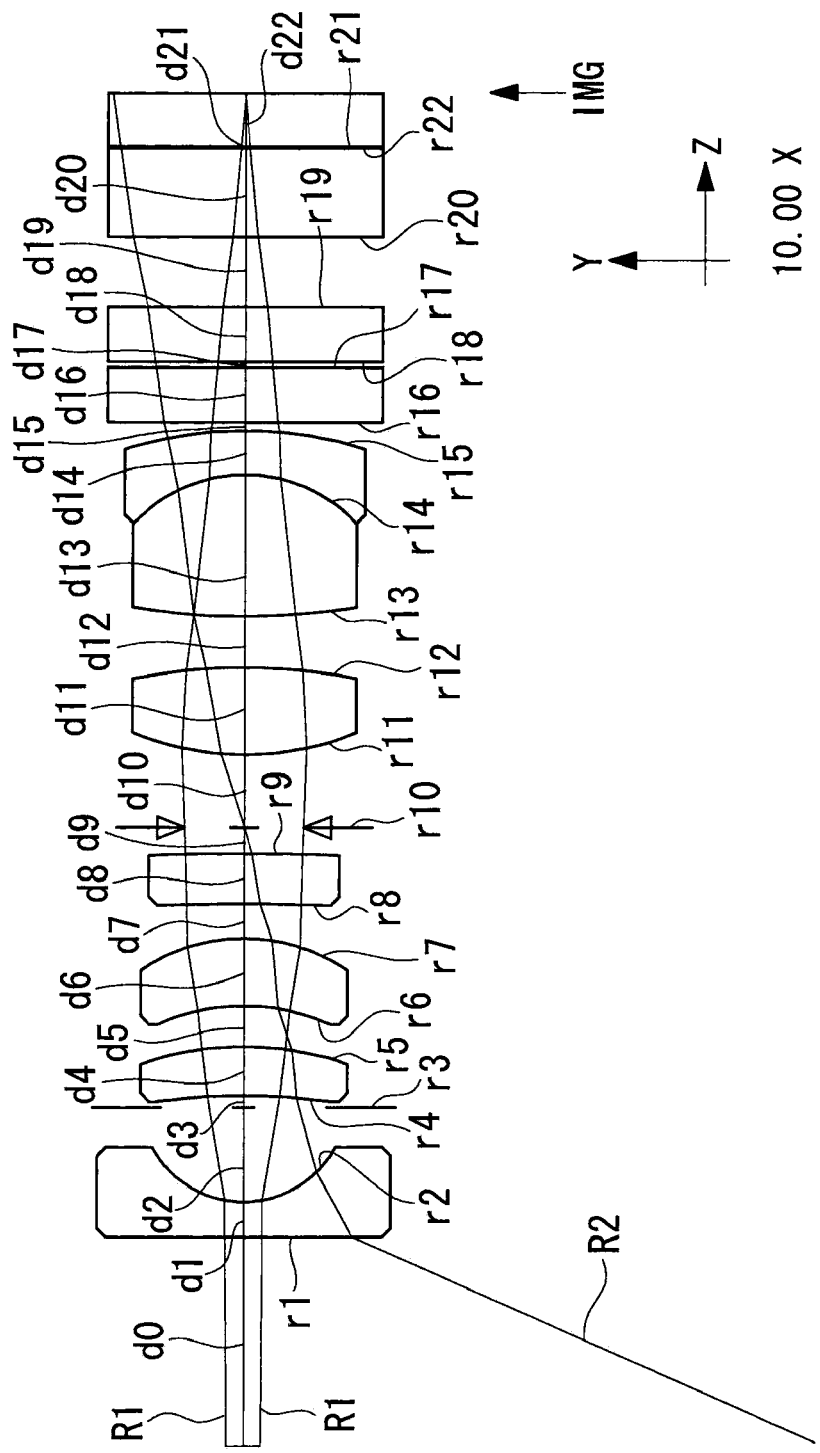
FIG. 15 is a lens cross-section showing the overall configuration (in the normal observation state) of an endoscope objective lens according to Example 5 of the present invention.

The lens configuration of an endoscope objective lens according to Example 5 of this embodiment is shown in FIG. 15.

In this example, the front group includes, in sequence from the object side, a plano-concave lens (first lens) having a flat surface facing the object side, a positive meniscus lens (second lens) having a concave surface facing the object side, and another positive meniscus lens having a concave surface facing the object side. The rear group includes, in sequence from the object side, two biconvex lenses and a negative meniscus lens having a concave surface facing the object side. In the rear group, the biconvex lens on the image side and the negative meniscus lens are combined.

The focusing lens (eighth surface) has a negative meniscus lens that has a concave surface facing the object side and that is inserted into or retracted from the optical path between the front group and the aperture stop.

Figure 16:
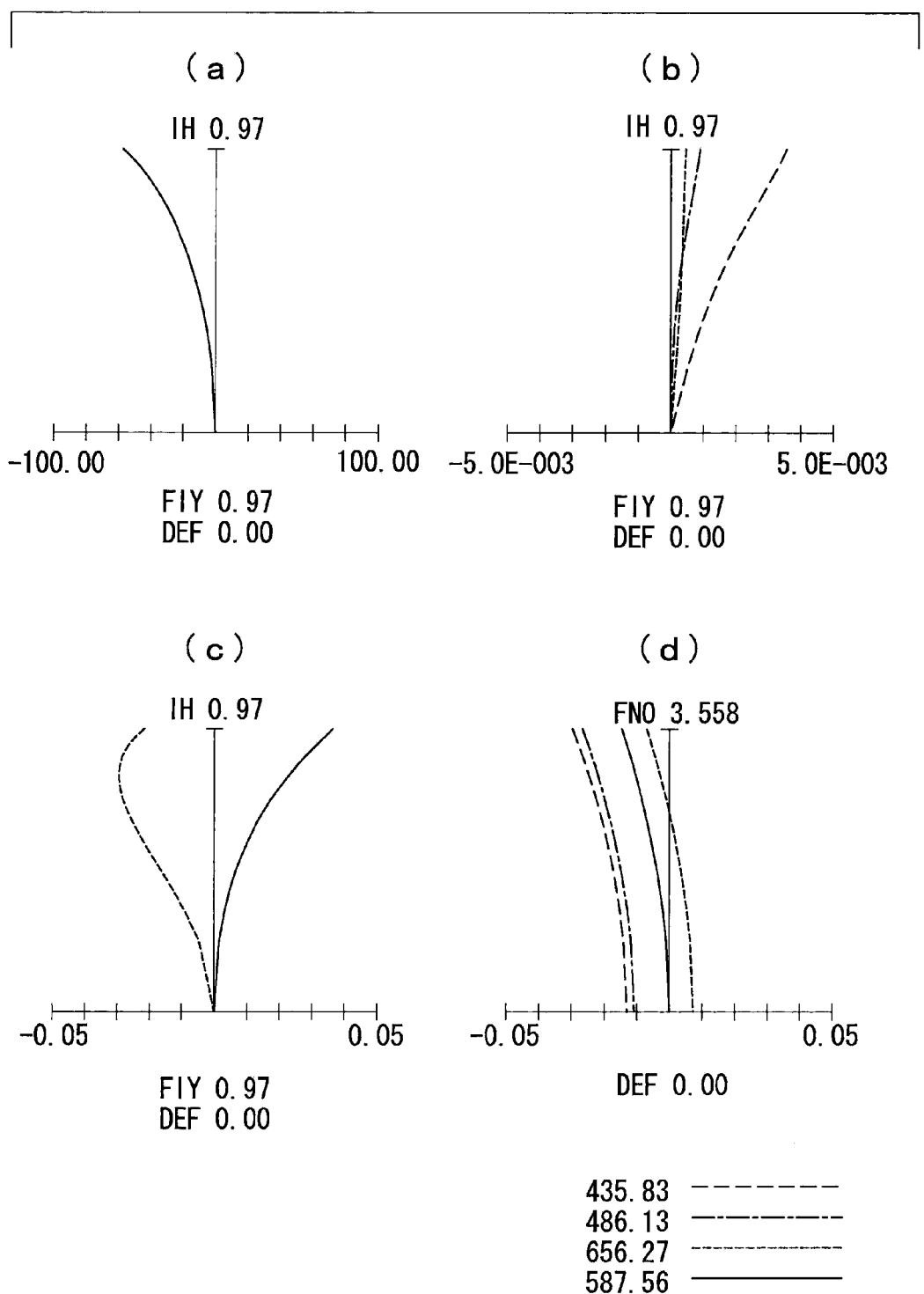
FIG. 16 includes aberration diagrams showing (a) distortion, (b) chromatic aberration of magnification, (c) astigmatism, and (d) spherical aberration, respectively, of the endoscope objective lens, in the normal observation state, according to Example 5 of the present invention.
Figure 17:
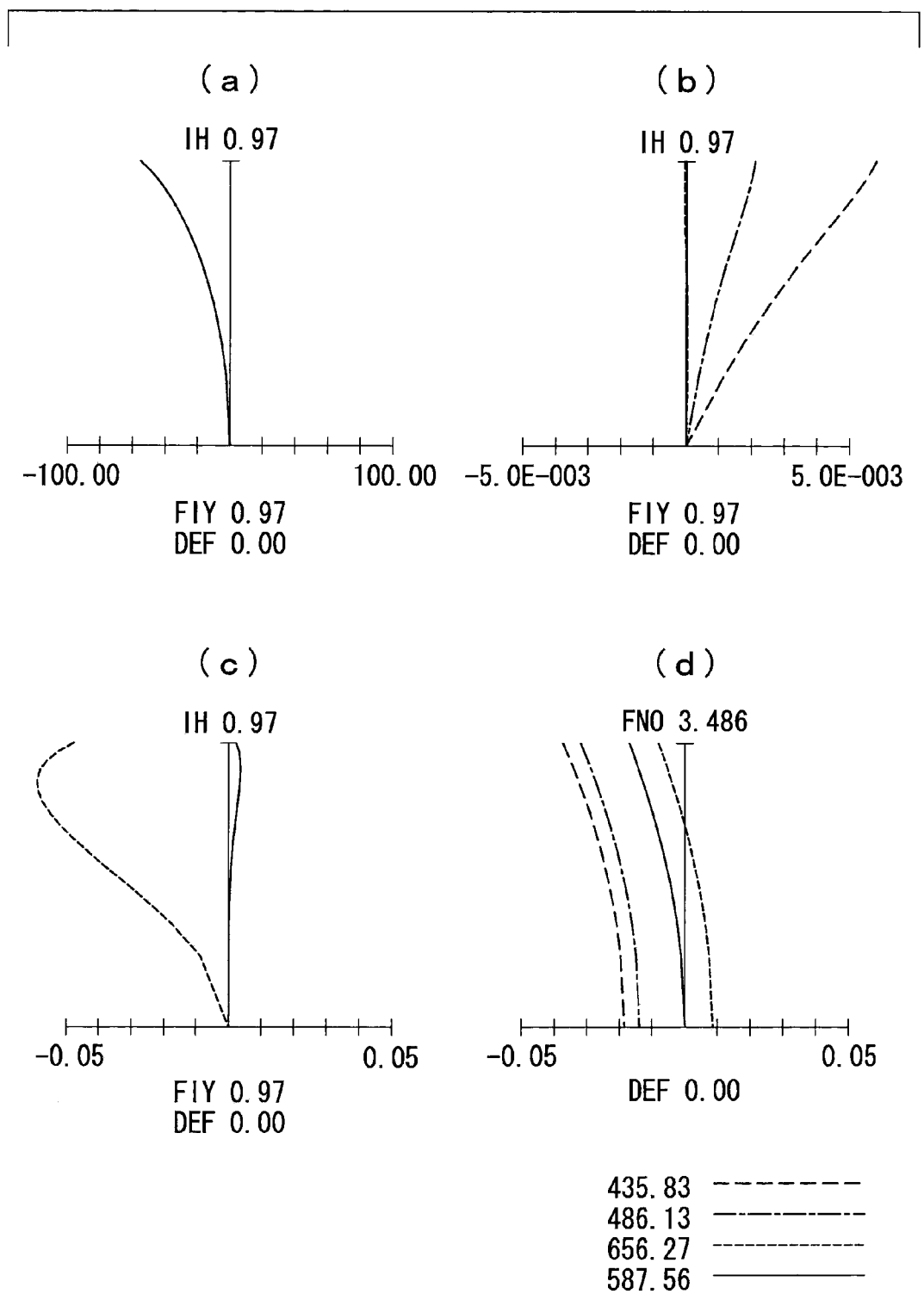
FIG. 17 includes aberration diagrams showing (a) distortion, (b) chromatic aberration of magnification, (c) astigmatism, and (d) spherical aberration, respectively, of the endoscope objective lens, in the short-distance observation state, according to Example 5 of the present invention.

The aberration diagrams of the thus-configured endoscope objective lens according to this example, in the normal observation state and in the short-distance observation state, are shown in FIGS. 16 and 17.

Lens Data

| surface number | r | d | nd | vd |
|---|---|---|---|---|
| OBJ | ∞ | 24.0000 (d0) | 1. | |
| 1 | ∞ | 0.2516 | 1.88300 | 40.76 |
| 2 | 0.7628 | 0.6775 | 1. | |
| 3 (FS) | ∞ | 0.0841 | 1. | |
| 4 | −4.3220 | 0.3485 | 1.88300 | 40.76 |
| 5 | −2.3317 | 0.2914 | 1. | |
| 6 | −1.5290 | 0.4841 | 1.88300 | 40.76 |
| 7 | −1.3410 | 0.2509 | 1. | |
| 8 | −14.1643 (r8) | 0.3607 | 1.88300 (GLA8) | 40.76 |
| 9 | −17.2905 (r9) | 0.1895 | 1. | |
| 10 (AS) | ∞ | 0.5222 | 1. | |
| 11 | 2.1889 | 0.6225 | 1.51823 | 58.90 |
| 12 | −4.1376 | 0.3633 | 1. | |
| 13 | 5.2905 | 1.0154 | 1.48749 | 70.23 |
| 14 | −1.1207 | 0.3145 | 1.92286 | 18.90 |
| 15 | −2.9312 | 0.0629 | 1. | |
| 16 (E) | ∞ | 0.3899 | 1.51400 | 75.00 |
| 17 | ∞ | 0.0377 | 1. | |
| 18 (E) | ∞ | 0.3899 | 1.52300 | 58.50 |
| 19 | ∞ | 0.5060 | 1. | |
| 20 (G1) | ∞ | 0.6289 | 1.51633 | 64.14 |
| 21 | ∞ | 0.0126 | 1.51300 | 63.01 |
| 22 (G2) | ∞ | 0.3773 | 1.50600 | 60.00 |
| IMG | ∞ | 0. | | |

Miscellaneous Data

| | normal observation state | short-distance observation state |
|---|---|---|
| d0 | 24.0000 | 7.0000 |
| r8 | −14.16429 | ∞ |
| r9 | −17.29047 | ∞ |
| GLA8 | nd: 1.88300 vd: 40.76 | air |

Example 6

Figure 18:
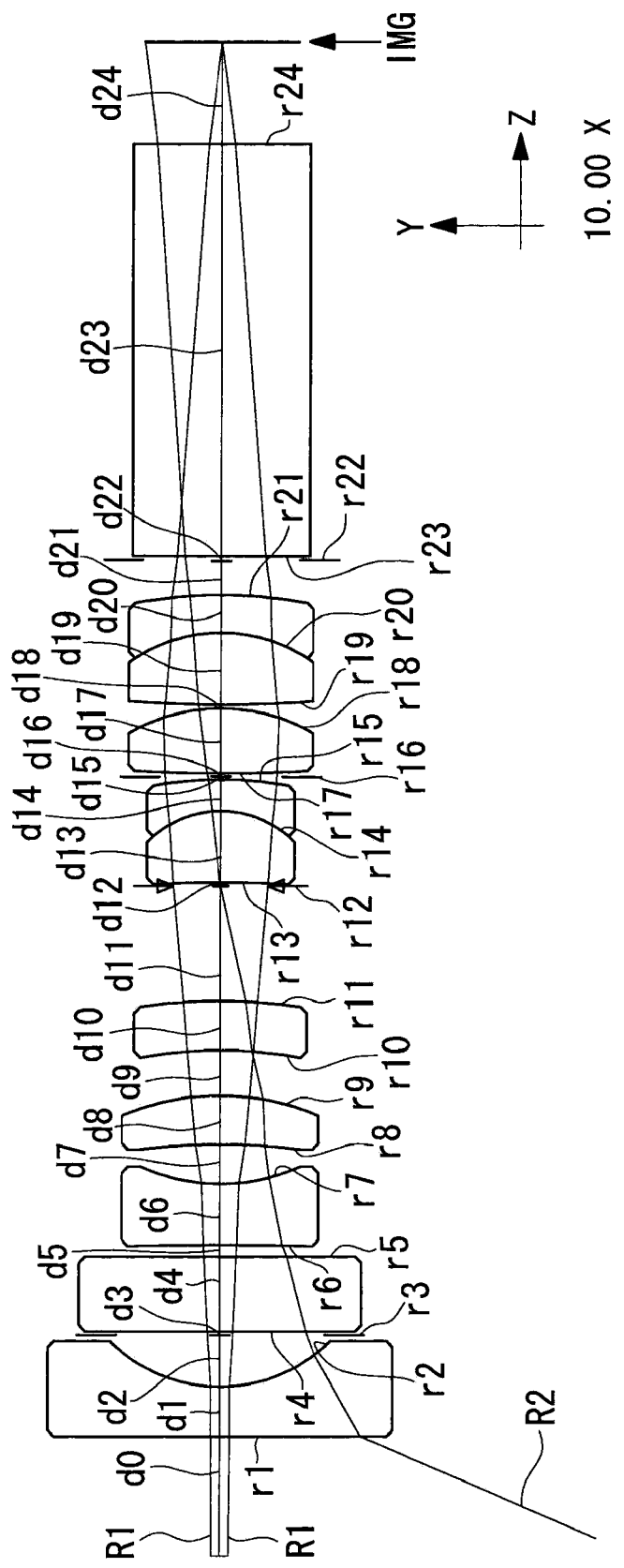
FIG. 18 is a lens cross-section showing the overall configuration (in the normal observation state) of an endoscope objective lens according to Example 6 of the present invention.

The lens configuration of an endoscope objective lens according to Example 6 of this embodiment is shown in FIG. 18.

In this example, the front group includes, in sequence from the object side, a plano-concave lens (first lens) having a flat surface facing the object side, a biconcave lens (second lens), and a positive meniscus lens having a concave surface facing the object side. An infrared cut filter, serving as an optical component E, is disposed between the plano-concave lens and the biconcave lens. The rear group includes, in sequence from the object side, a positive meniscus lens having a concave surface facing the object side, a negative meniscus lens having a concave surface facing the object side, two biconvex lenses, and a negative meniscus lens having a concave surface facing the object side. In the rear group, the positive meniscus lens on the object side and the negative meniscus lens are combined, and the biconvex lens on the image side and the negative meniscus lens are combined. A component corresponding to the twenty-third surface is an optical prism PL.

The focusing lens (tenth surface) includes a negative meniscus lens that has a concave surface facing the object side and that is inserted into or retracted from the optical path between the front group and the aperture stop.

Figure 19:
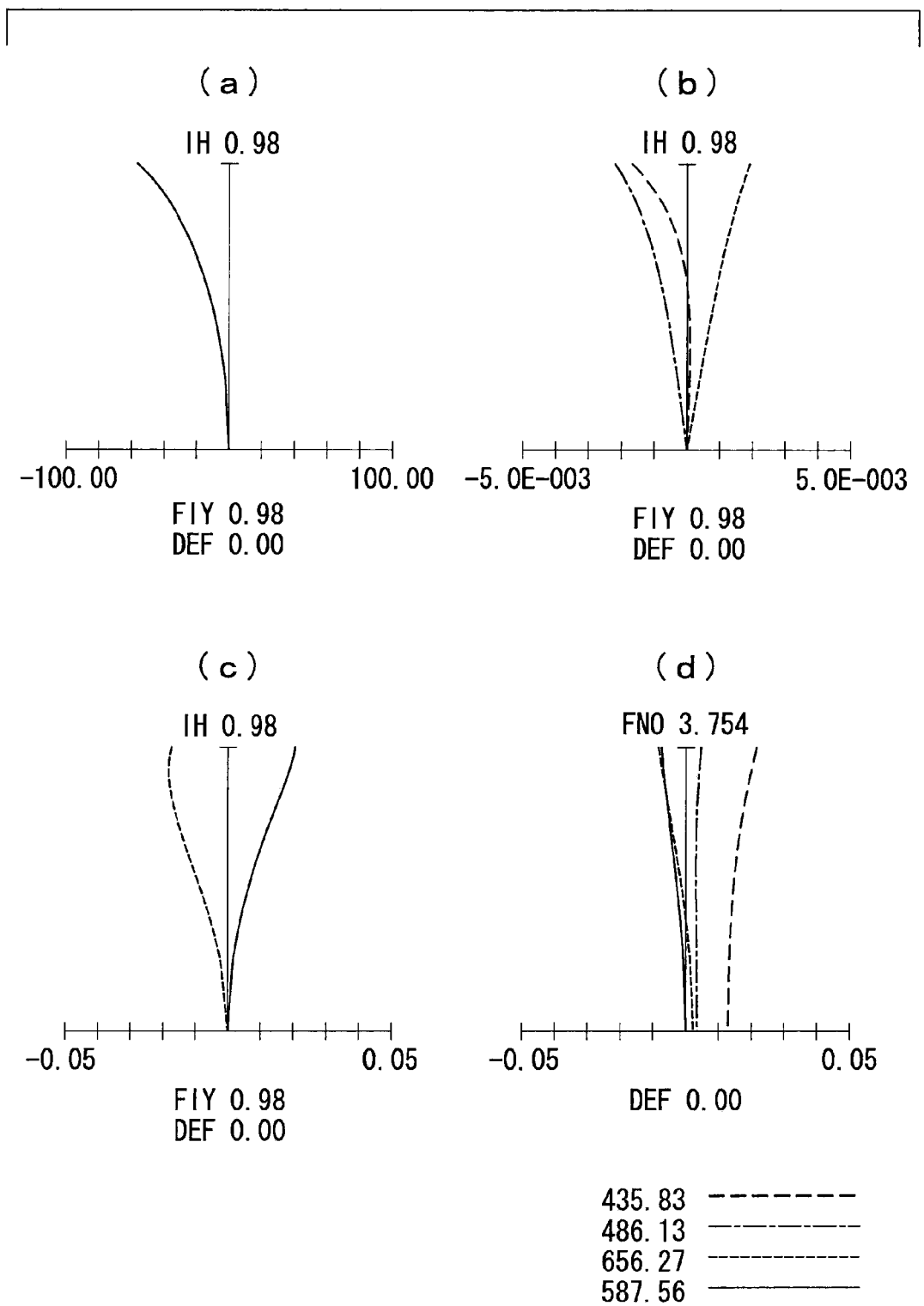
FIG. 19 includes aberration diagrams showing (a) distortion, (b) chromatic aberration of magnification, (c) astigmatism, and (d) spherical aberration, respectively, of the endoscope objective lens, in the normal observation state, according to Example 6 of the present invention.
Figure 20:
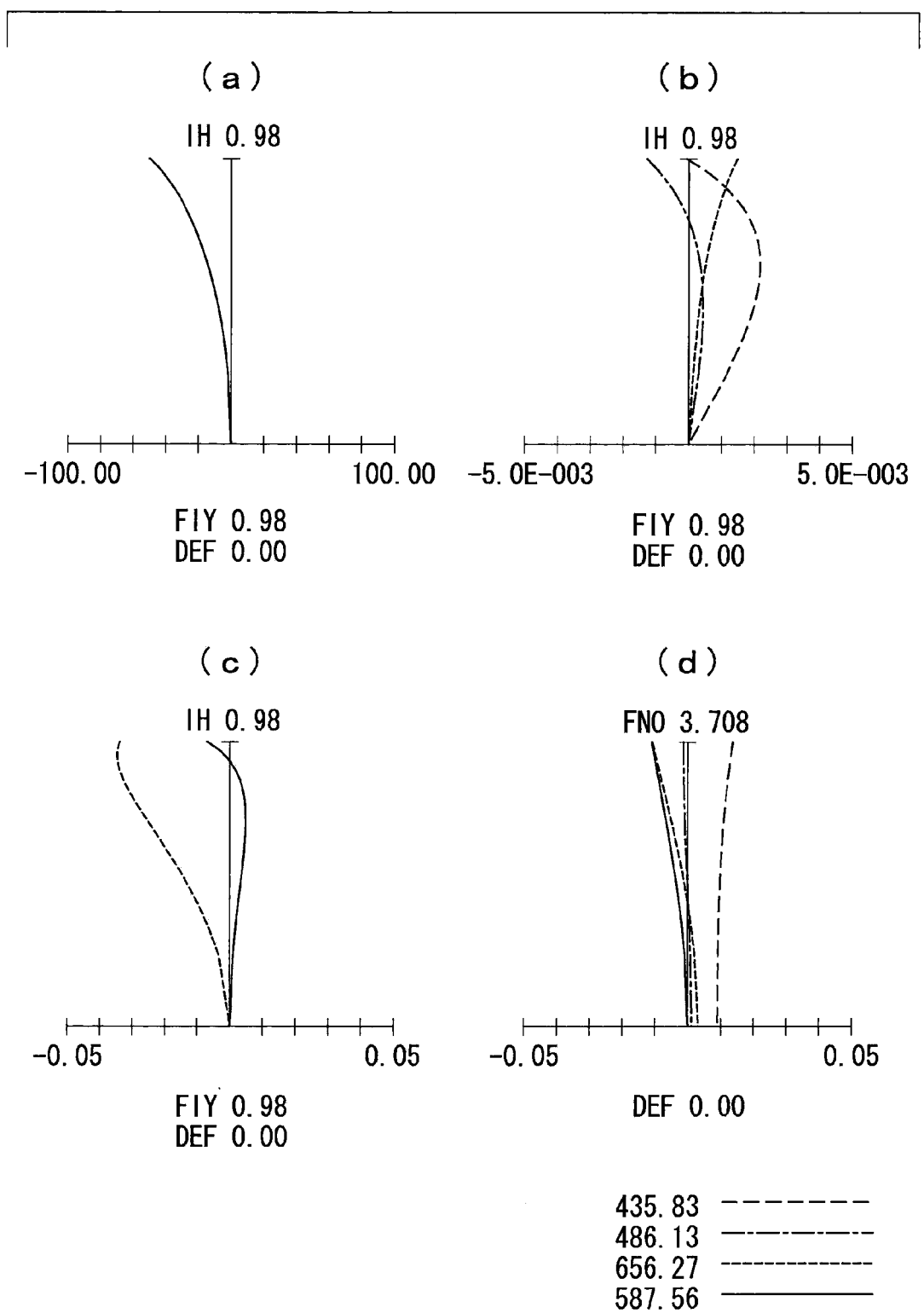
FIG. 20 includes aberration diagrams showing (a) distortion, (b) chromatic aberration of magnification, (c) astigmatism, and (d) spherical aberration, respectively, of the endoscope objective lens, in the short-distance observation state, according to Example 6 of the present invention.

The aberration diagrams of the thus-configured endoscope objective lens according to this example, in the normal observation state and in the short-distance observation state, are shown in FIGS. 19 and 20.

Lens Data

| surface number | r | d | nd | vd |
|---|---|---|---|---|
| OBJ | ∞ | 19.7000 (d0) | 1. | |
| 1 | ∞ | 0.6278 | 1.88300 | 40.76 |
| 2 | 2.0066 | 0.6489 | 1. | |
| 3 (FS) | ∞ | 0.0471 | 1. | |
| 4 (E) | ∞ | 0.9417 | 1.51800 | 75.00 |
| 5 | ∞ | 0.1473 | 1. | |
| 6 | −36.9819 | 0.7582 | 1.88300 | 40.76 |
| 7 | 2.4930 | 0.4976 | 1. | |
| 8 | −7.9998 | 0.6090 | 1.92286 | 18.90 |
| 9 | −3.2815 | 0.5733 | 1. | |
| 10 | −5.6123 (r10) | 0.6240 | 1.51633 (GLA10) | 64.14 |
| 11 | −6.9299 (r11) | 1.4464 | 1. | |
| 12 (AS) | ∞ | 0.0471 | 1. | |
| 13 | −15.5514 | 0.8969 | 1.84666 | 23.78 |
| 14 | −1.3261 | 0.3924 | 2.00330 | 28.27 |
| 15 | −4.7763 | 0.0314 | 1. | |
| 16 (FS) | ∞ | 0.0471 | 1. | |
| 17 | 22.5970 | 0.8137 | 1.48749 | 70.23 |
| 18 | −2.3801 | 0.0471 | 1. | |
| 19 | 15.6900 | 0.9006 | 1.58913 | 61.14 |
| 20 | −2.0398 | 0.4708 | 1.92286 | 18.90 |
| 21 | −5.9644 | 0.4377 | 1. | |
| 22 (FS) | ∞ | 0.0471 | 1. | |
| 23 (PL) | ∞ | 5.1529 | 1.72916 | 54.68 |
| 24 | ∞ | 1.2712 | 1. | |
| IMG | ∞ | 0. | | |

Miscellaneous Data

| | normal observation state | short-distance observation state |
|---|---|---|
| d0 | 19.7000 | 4.9000 |
| r10 | −5.61226 | ∞ |
| r11 | −6.92989 | ∞ |
| GLA10 | nd: 1.51633 vd: 64.14 | air |

Example 7

Figure 21:
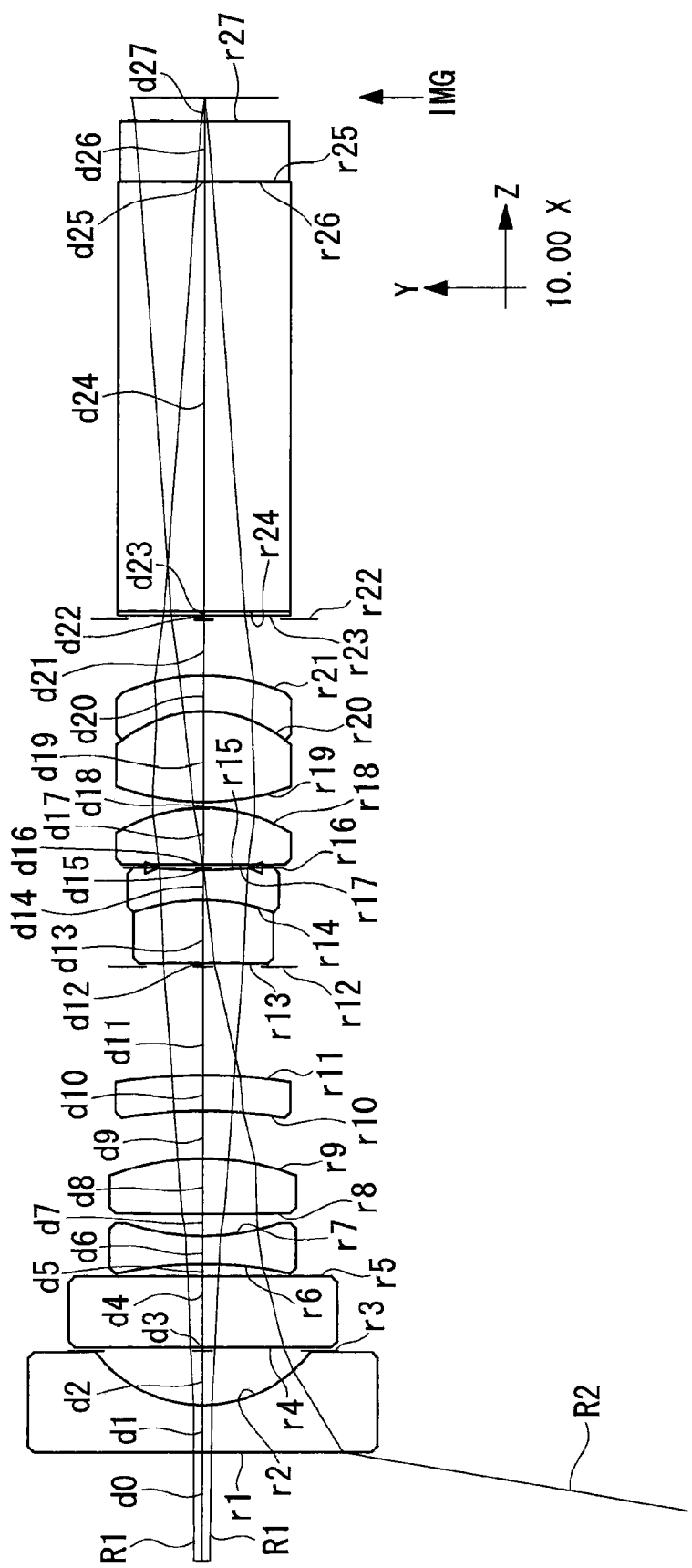
FIG. 21 is a lens cross-section showing the overall configuration (in the normal observation state) of an endoscope objective lens according to Example 7 of the present invention.

The lens configuration of an endoscope objective lens according to Example 7 of this embodiment is shown in FIG. 21.

In this example, the front group includes, in sequence from the object side, a plano-concave lens (first lens) having a flat surface facing the object side, a biconcave lens (second lens), and a biconvex lens. An infrared cut filter, serving as an optical component E, is disposed between the plano-concave lens and the biconcave lens. The rear group includes, in sequence from the object side, a positive meniscus lens having a concave surface facing the object side, a biconcave lens, a plano-convex lens having a flat surface facing the object plane, a biconvex lens, and a negative meniscus lens having a concave surface facing the object side. In the rear group, the positive meniscus lens on the object side and the biconcave lens are combined, and the biconvex lens on the image side and the negative meniscus lens are combined. The aperture stop may be disposed on the object side of the positive meniscus lens.

The focusing lens (tenth surface) is a negative meniscus lens that has a concave surface facing the object side and that is inserted into or retracted from the optical path between the front group and the rear group.

Figure 22:
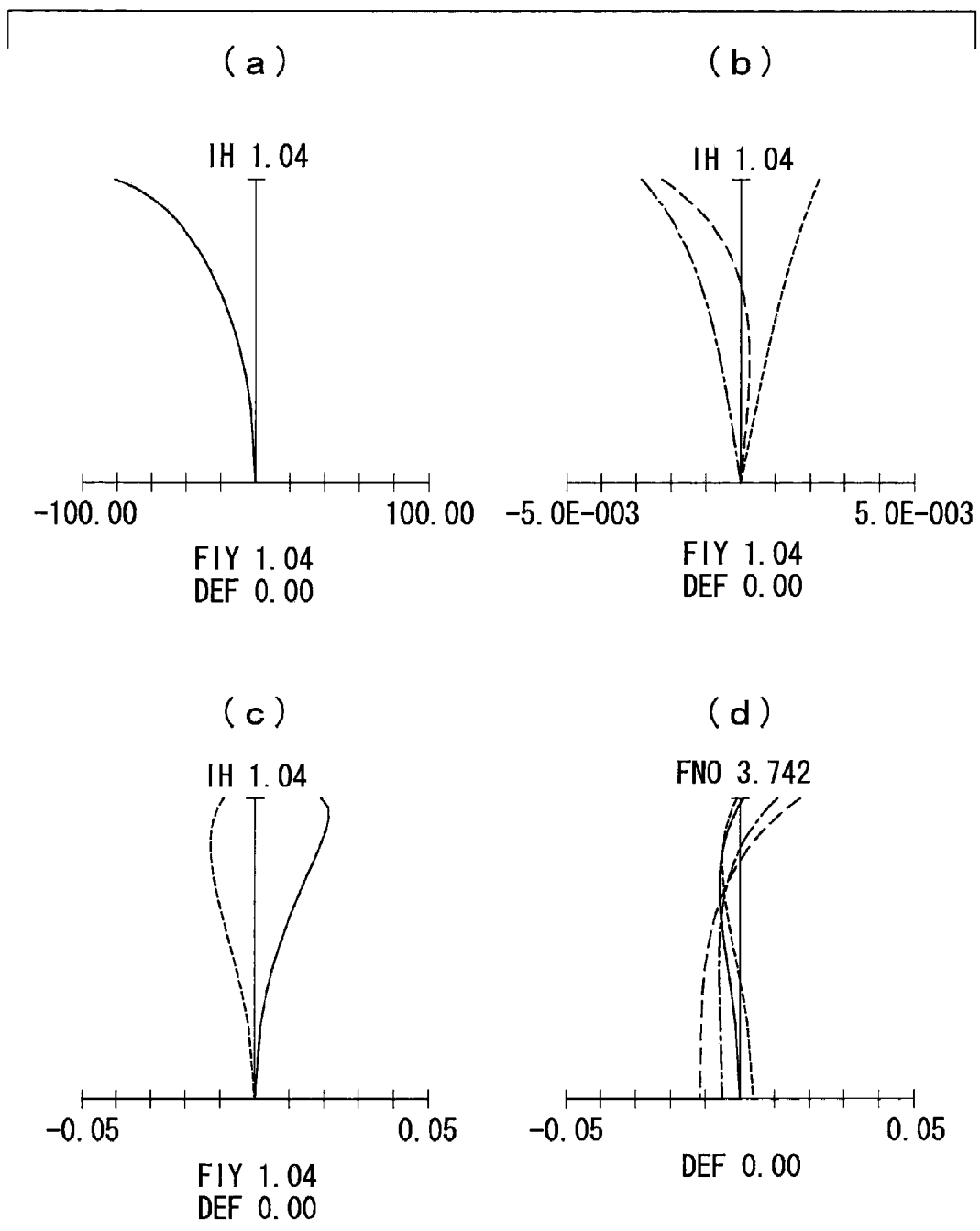
FIG. 22 includes aberration diagrams showing (a) distortion, (b) chromatic aberration of magnification, (c) astigmatism, and (d) spherical aberration, respectively, of the endoscope objective lens, in the normal observation state, according to Example 7 of the present invention.
Figure 23:
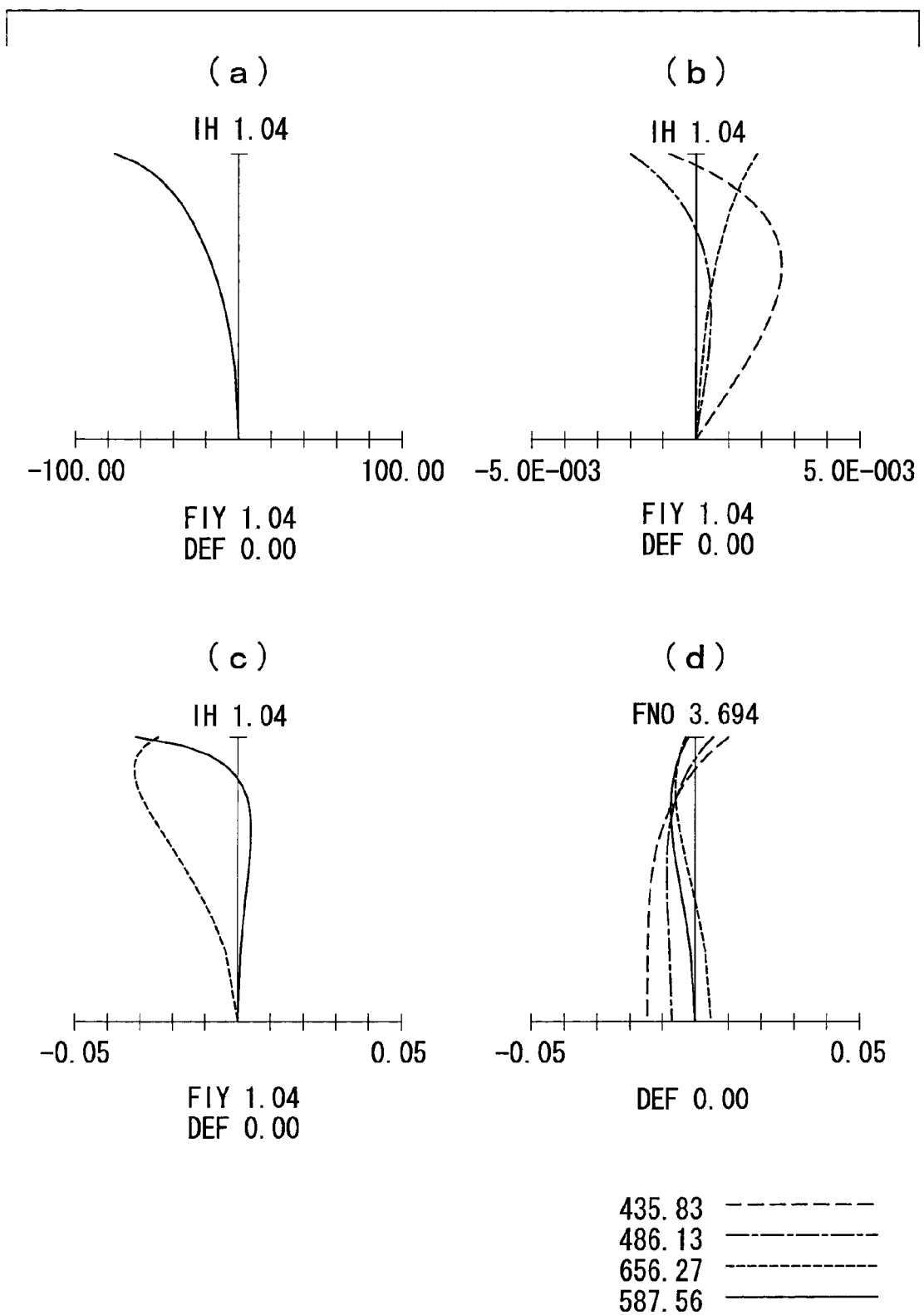
FIG. 23 includes aberration diagrams showing (a) distortion, (b) chromatic aberration of magnification, (c) astigmatism, and (d) spherical aberration, respectively, of the endoscope objective lens, in the short-distance observation state, according to Example 7 of the present invention.

The aberration diagrams of the thus-configured endoscope objective lens according to this example, in the normal observation state and in the short-distance observation state, are shown in FIGS. 22 and 23.

Lens Data

| surface number | r | d | nd | vd |
|---|---|---|---|---|
| OBJ | ∞ | 21.0000 (d0) | 1. | |
| 1 | ∞ | 0.6623 | 1.88300 | 40.76 |
| 2 | 1.9404 | 0.7629 | 1. | |
| 3 (FS) | ∞ | 0.0497 | 1. | |
| 4 (E) | ∞ | 0.9935 | 1.51800 | 75.00 |
| 5 | ∞ | 0.1714 | 1. | |
| 6 | −5.6800 | 0.3893 | 1.88300 | 40.76 |
| 7 | 3.4284 | 0.3104 | 1. | |
| 8 | 94.6110 | 0.7739 | 1.92286 | 18.90 |
| 9 | −3.7903 | 0.6623 | 1. | |
| 10 | −7.1402 (r10) | 0.4967 | 1.88300 (GLA10) | 40.76 |
| 11 | −8.2872 (r11) | 1.5233 | 1. | |
| 12 (FS) | ∞ | 0.0497 | 1. | |
| 13 | −63.3015 | 0.8867 | 1.92286 | 18.90 |
| 14 | −2.8981 | 0.4139 | 2.00330 | 28.27 |
| 15 | 8.3149 | 0.0331 | 1. | |
| 16 (AS) | ∞ | 0.0497 | 1. | |
| 17 | ∞ | 0.7858 | 1.48749 | 70.23 |
| 18 | −2.3952 | 0.0828 | 1. | |
| 19 | 3.6431 | 1.2605 | 1.48749 | 70.23 |
| 20 | −1.8890 | 0.4967 | 1.92286 | 18.90 |
| 21 | −2.9467 | 0.7933 | 1. | |
| 22 (FS) | ∞ | 0.0497 | 1. | |
| 23 (E) | ∞ | 0.0546 | 1.53000 | 56.00 |
| 24 (PL) | ∞ | 5.9741 | 1.72916 | 54.68 |
| 25 | ∞ | 0.0166 | 1.51000 | 64.00 |
| 26 (G2) | ∞ | 0.8279 | 1.61062 | 50.49 |
| 27 | ∞ | 0.3312 | 1. | |
| IMG | ∞ | 0. | | |

Miscellaneous Data

| | normal observation state | short-distance observation state |
|---|---|---|
| d0 | 21.0000 | 5.1000 |
| r10 | −7.14017 | ∞ |
| r11 | −8.28720 | ∞ |
| GLA10 | nd: 1.88300 vd: 40.76 | air |

Example 8

Figure 24:
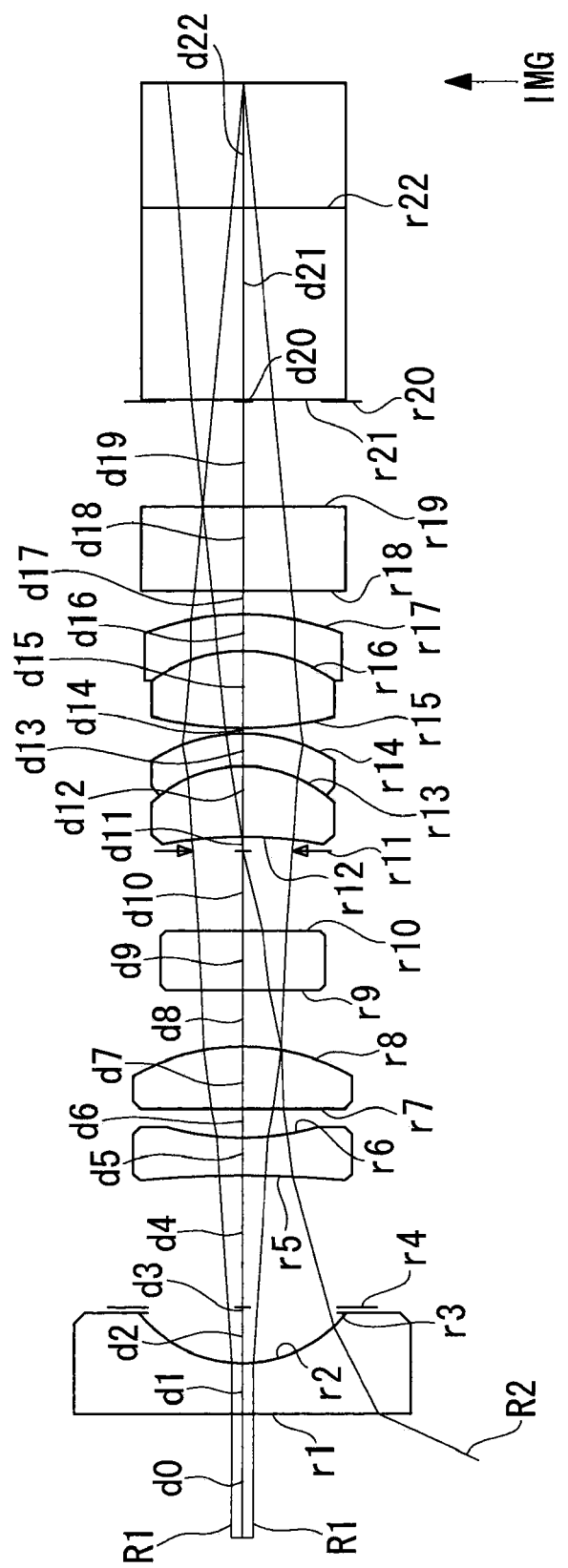
FIG. 24 is a lens cross-section showing the overall configuration (in the normal observation state) of an endoscope objective lens according to Example 8 of the present invention.

The lens configuration of an endoscope objective lens according to Example 8 of this embodiment is shown in FIG. 24.

In this example, the front group includes, in sequence from the object side, a plano-concave lens (first lens) having a flat surface facing the object side, a biconcave lens (second lens), and a meniscus lens. The rear group includes two combined lenses. An infrared cut filter, serving as an optical component E, is disposed on the image side of these combined lenses.

The focusing lens (ninth surface) is a plano-concave lens that has a flat surface facing the image side and that is inserted into or retracted from the optical path between the front group and the rear group.

Figure 25:
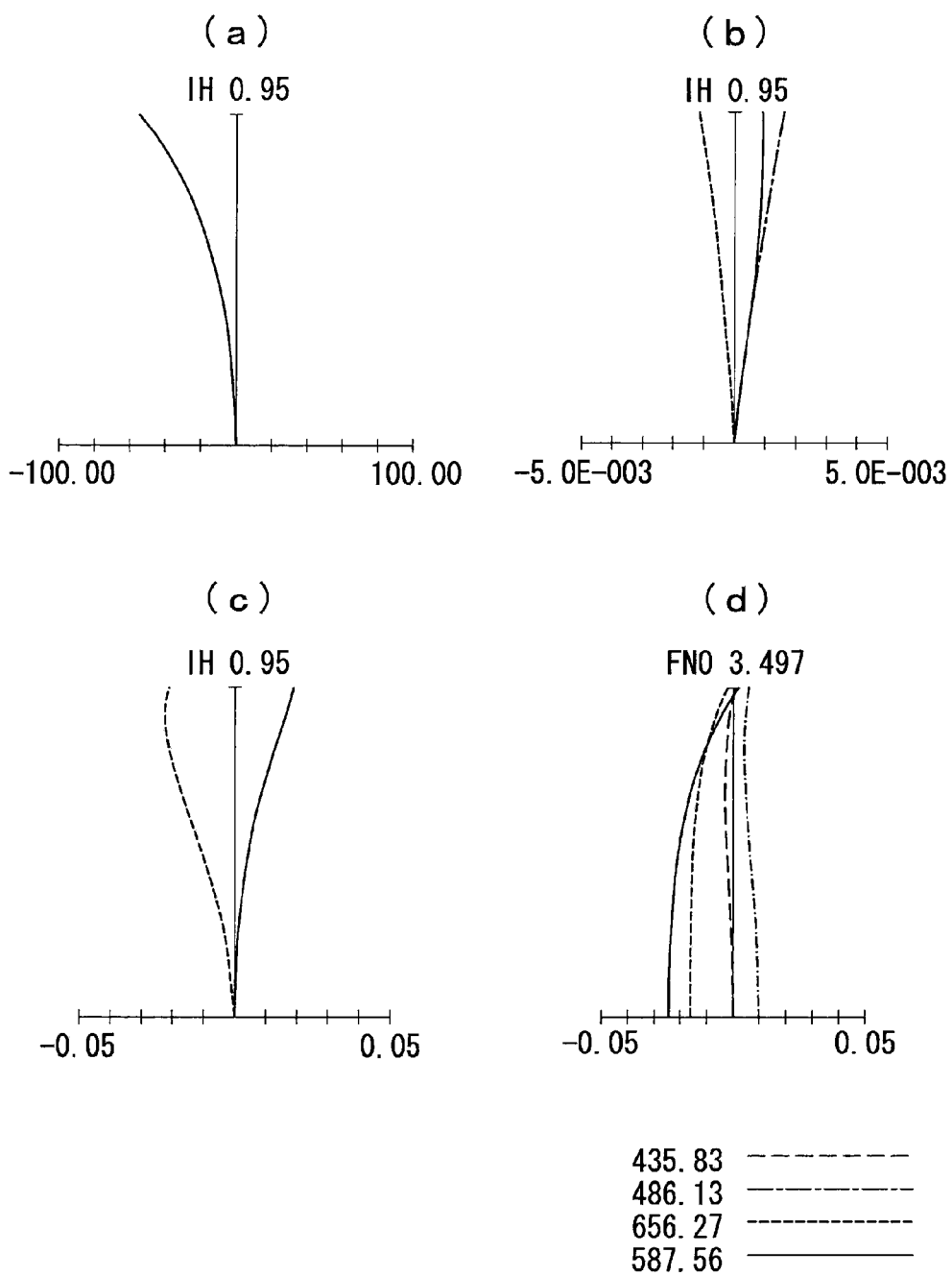
FIG. 25 includes aberration diagrams showing (a) distortion, (b) chromatic aberration of magnification, (c) astigmatism, and (d) spherical aberration, respectively, of the endoscope objective lens, in the normal observation state, according to Example 8 of the present invention.
Figure 26:
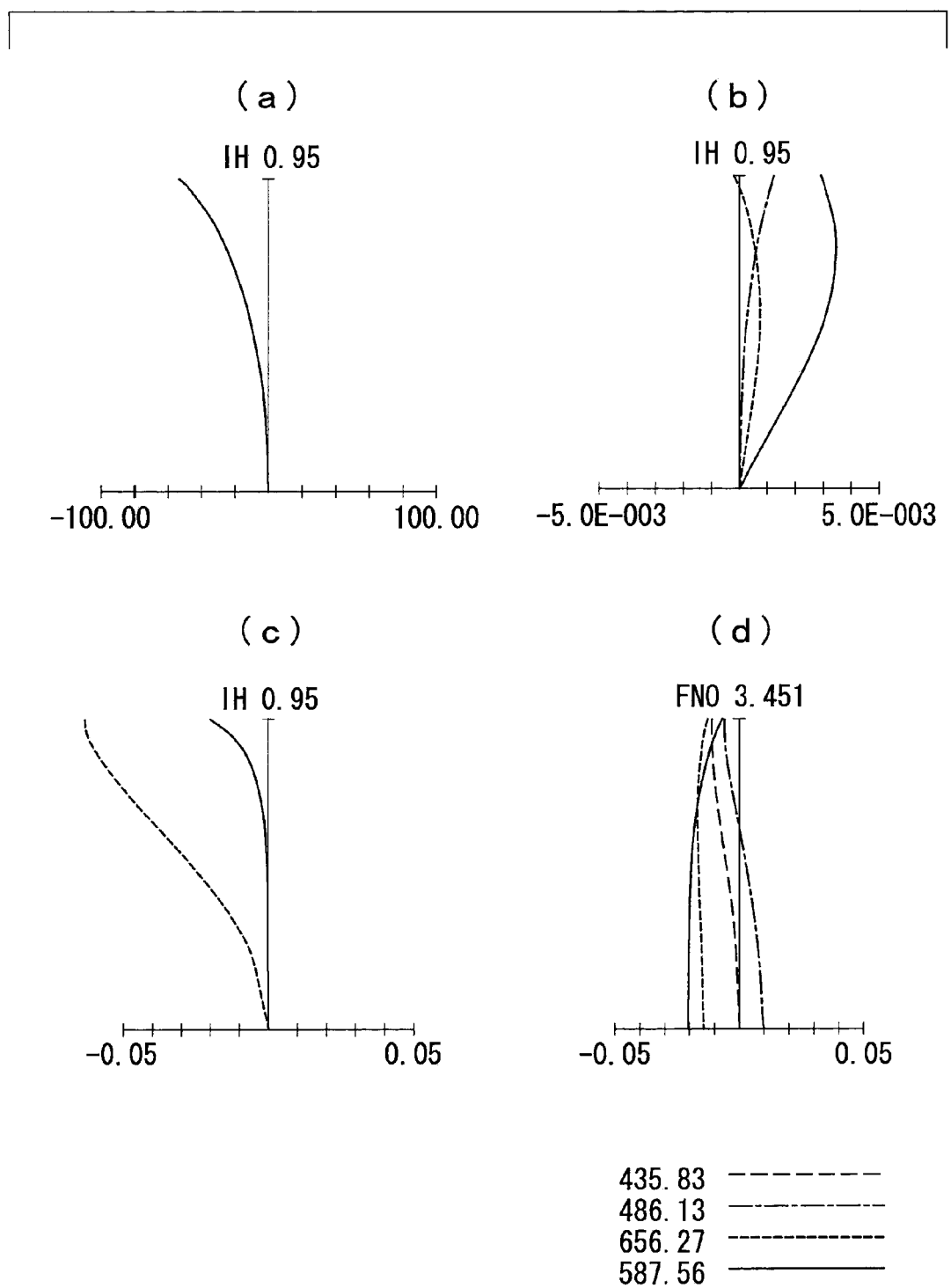
FIG. 26 includes aberration diagrams showing (a) distortion, (b) chromatic aberration of magnification, (c) astigmatism, and (d) spherical aberration, respectively, of the endoscope objective lens, in the short-distance observation state, according to Example 8 of the present invention.

The aberration diagrams of the thus-configured endoscope objective lens according to this example, in the normal observation state and in the short-distance observation state, are shown in FIGS. 25 and 26.

Lens Data

| surface number | r | d | nd | vd |
|---|---|---|---|---|
| OBJ | ∞ | 20.8000 (d0) | 1. | |
| 1 | ∞ | 0.6090 | 1.88300 | 40.76 |
| 2 | 1.7677 | 1.1244 | 1. | |
| 3 (FS) | ∞ | 0.0459 | 1. | |
| 4 | ∞ | 1.1218 | 1. | |
| 5 | −6.7859 | 0.4546 | 1.88300 | 40.76 |
| 6 | 3.4679 | 0.3788 | 1. | |
| 7 | −34.9131 | 0.7425 | 1.92286 | 18.90 |
| 8 | −3.0411 | 0.6829 | 1. | |
| 9 | −108.8804 (r9) | 0.7184 | 1.51633 (GLA9) | 64.14 |
| 10 | ∞ (r10) | 0.9804 | 1. | |
| 11 (AS) | ∞ | 0.1515 | 1. | |
| 12 | −10.7619 | 0.8940 | 1.53172 | 48.84 |
| 13 | −1.6970 | 0.3788 | 2.00330 | 28.27 |

-continued

| surface number | r | d | nd | vd |
|---|---|---|---|---|
| 14 | −2.2508 | 0.0758 | 1. | |
| 15 | 5.4666 | 0.9092 | 1.48749 | 70.23 |
| 16 | −2.1303 | 0.4546 | 1.92286 | 18.90 |
| 17 | −3.6797 | 0.2995 | 1. | |
| 18 (E) | ∞ | 0.9983 | 1.51633 | 64.14 |
| 19 | ∞ | 1.2678 | 1. | |
| 20 (FS) | ∞ | 0.0399 | 1. | |
| 21 (G1) | ∞ | 2.3161 | 1.51633 | 64.14 |
| 22 (G2) | ∞ | 1.4975 | 1.61062 | 50.49 |
| IMG | ∞ | 0. | | |

Miscellaneous Data

| | normal observation state | short-distance observation state |
|---|---|---|
| d0 | 20.8000 | 4.7100 |
| r9 | −108.8804 | ∞ |
| r10 | ∞ | ∞ |
| GLA9 | nd: 1.51633 vd: 64.14 | air |

Regarding the endoscope objective lens according to Examples 1 to 8 of this embodiment, the values corresponding to Conditional Expressions (1) to (6) are shown in Table 1, and the specifications are shown in Table 2. In Tables 1 and 2, FL is the focal length of the entire endoscope objective lens in the normal observation state, $2\omega$ is the angle of view (unit: deg), IH is the image height, f_F is the focal length of the front group, f_R is the focal length of the rear group, fc is the focal length of the focusing lens, ra is the radius of curvature of the object-side surface of the focusing lens, rb is the radius of curvature of the image-side surface of the focusing lens, r1b is the radius of curvature of the image-side surface of the first lens, and r2f is the radius of curvature of the object-side surface of the second lens.

TABLE 1

| Conditional Expression | Example 1 | Example 2 | Example 3 | Example 4 | Example 5 | Example 6 | Example 7 | Example 8 |
|---|---|---|---|---|---|---|---|---|
| (1) fc/FL | −112.539 | −77.056 | −71.783 | −57.003 | −93.796 | −68.158 | −73.311 | −210.874 |
| (2) (rb + ra)/(rb − ra) | 7.870 | 13.100 | 1.000 | 14.908 | 10.062 | 9.519 | 13.450 | 1.000 |
| (3) ra/FL | −21.760 | −8.649 | −34.994 | −5.613 | −14.164 | −5.612 | −7.140 | −108.880 |
| (4) (r2f + r1b)/(r2f − r1b) | 0.840 | 0.456 | 0.662 | 0.745 | 0.700 | 0.897 | 0.491 | 0.587 |
| (5) r2f/FL | −15.413 | −2.964 | −5.576 | −7.276 | −4.322 | −36.982 | −5.680 | −6.786 |
| (6) r1b/FL | 1.337 | 1.108 | 1.135 | 1.065 | 0.763 | 2.007 | 1.940 | 1.768 |

TABLE 2

| | | Example 1 | Example 2 | Example 3 | Example 4 | Example 5 | Example 6 | Example 7 | Example 8 |
|---|---|---|---|---|---|---|---|---|---|
| FL | normal observation state | 1.000 | 1.000 | 1.000 | 1.000 | 1.000 | 1.000 | 1.000 | 1.000 |
| | short-distance observation state | 0.987 | 0.990 | 0.983 | 0.986 | 0.983 | 0.994 | 0.996 | 0.969 |
| effective Fno. | normal observation state | 3.009 | 3.412 | 3.415 | 3.326 | 3.592 | 3.776 | 3.763 | 3.517 |
| | short-distance observation state | 3.010 | 3.412 | 3.417 | 3.328 | 3.593 | 3.780 | 3.765 | 3.520 |
| 2ω | normal observation state | 137.6 | 137.6 | 140.4 | 140.7 | 132.6 | 133.7 | 161.0 | 130.1 |
| | short-distance observation state | 138.7 | 137.7 | 141.0 | 140.9 | 132.0 | 132.3 | 159.0 | 135.4 |
| IH | | 1.001 | 0.963 | 1.028 | 0.993 | 0.966 | 0.982 | 1.037 | 0.949 |
| f_F | | −3.901 | −3.160 | −4.783 | −2.307 | −5.730 | −1.648 | −1.915 | −2.424 |
| f_R | | 2.609 | 2.467 | 2.156 | 2.034 | 2.678 | 3.309 | 3.469 | 3.476 |
| fc | | −112.539 | −77.056 | −71.783 | −57.003 | −93.796 | −68.158 | −73.311 | −210.874 |

TABLE 2-continued

|     | Example 1 | Example 2 | Example 3 | Example 4 | Example 5 | Example 6 | Example 7 | Example 8 |
|-----|-----------|-----------|-----------|-----------|-----------|-----------|-----------|-----------|
| ra  | −21.7597  | −8.6485   | −34.9936  | −5.6126   | −14.1643  | −5.6123   | −7.1402   | −108.8804 |
| rb  | −28.0944  | −10.078   | ∞         | −6.4197   | −17.2905  | −6.9299   | −8.2872   | ∞         |
| r1b | 1.3366    | 1.1077    | 1.1348    | 1.0649    | 0.7628    | 2.0066    | 1.9404    | 1.7677    |
| r2f | −15.4125  | −2.9644   | −5.5758   | −7.2757   | −4.3220   | −36.9819  | −5.6800   | −6.7859   |

REFERENCE SIGNS LIST

1 endoscope objective lens
2 arm member
3 lens barrel
GF front group
GR rear group
AS aperture stop
Lf focusing lens
L1 first lens
L2 second lens
E optical component
FS flare stop
G1 CCD cover glass
G2 CCD chip sealing glass
R1 axial marginal ray
R2 principal ray at the maximum angle of view
WD working distance
OBJ object plane
IMG image plane

The invention claimed is:

1. An endoscope objective lens comprising:
in sequence from an object side, a front group having negative refractive power, an aperture stop, and a rear group having positive refractive power; and
a focusing lens that has negative refractive power and that can be inserted into or retracted from an optical path between the front group and the rear group,
wherein the focusing lens is inserted into the optical path in a normal observation state and is retracted from the optical path in a short-distance observation state, in which the working distance is smaller than that in the normal observation state, and
wherein Conditional Expressions (1), (2) and (3) below are satisfied:

$$-230 < fc/FL < -10 \quad (1)$$

$$0.7 < (rb+ra)/(rb-ra) < 20 \quad (2)$$

$$-120 < ra/FL < -3 \quad (3)$$

where fc is a focal length of the focusing lens, FL is a focal length of the entire endoscope objective lens in the normal observation state, ra is a radius of curvature of an object-side surface of the focusing lens, and rb is a radius of curvature of an image-side surface of the focusing lens.

2. The endoscope objective lens according to claim 1, wherein
the front group includes, in sequence from the object side, a first lens having a concave surface facing an image side, and a second lens having a concave surface facing the object side, and
Conditional Expressions (4), (5), (6) below are satisfied:

$$0.25 < (r2f+r1b)/(r2f-r1b) < 1 \quad (4)$$

$$-50 < r2f/FL < -2 \quad (5)$$

$$0.5 < r1b/FL < 3 \quad (6)$$

where r2f is a radius of curvature of an object-side surface of the second lens, and r1b is a radius of curvature of an image-side surface of the first lens.

3. The endoscope objective lens according to claim 1, wherein the focusing lens is a molded lens.

4. The endoscope objective lens according to claim 3, further comprising an arm member that supports the focusing lens and that moves the focusing lens between an inserted position where the focusing lens is inserted in the optical path and a retracted position where the focusing lens is retracted from the optical path, the arm member being molded integrally with the focusing lens.

* * * * *